United States Patent
Kobayashi

(10) Patent No.: US 9,963,686 B2
(45) Date of Patent: May 8, 2018

(54) MODIFIED DNA POLYMERASE

(71) Applicant: TOYOBO CO., LTD., Osaka-shi, Osaka (JP)

(72) Inventor: Tetsuhiro Kobayashi, Tsuruga (JP)

(73) Assignee: TOYOBO CO., LTD., Osaka (JP)

(*) Notice: Subject to any disclaimer, the term of this patent is extended or adjusted under 35 U.S.C. 154(b) by 12 days.

(21) Appl. No.: 14/422,448

(22) PCT Filed: Sep. 27, 2013

(86) PCT No.: PCT/JP2013/076217
§ 371 (c)(1),
(2) Date: Feb. 19, 2015

(87) PCT Pub. No.: WO2014/051031
PCT Pub. Date: Apr. 3, 2014

(65) Prior Publication Data
US 2015/0218534 A1   Aug. 6, 2015

(30) Foreign Application Priority Data

Sep. 28, 2012 (JP) ................. 2012-217474
Sep. 28, 2012 (JP) ................. 2012-217475
Mar. 29, 2013 (JP) ................. 2013-072515
Mar. 29, 2013 (JP) ................. 2013-072516
Mar. 29, 2013 (JP) ................. 2013-072517

(51) Int. Cl.
| C12N 9/12 | (2006.01) |
| C12P 19/34 | (2006.01) |
| C12N 15/00 | (2006.01) |
| C12N 1/20 | (2006.01) |
| C07H 21/04 | (2006.01) |
| C12P 21/06 | (2006.01) |
| C12P 21/04 | (2006.01) |
| C12N 15/09 | (2006.01) |

(52) U.S. Cl.
CPC ......... *C12N 9/1241* (2013.01); *C12N 9/1252* (2013.01); *C12N 15/09* (2013.01); *C12P 19/34* (2013.01); *C12Y 207/07007* (2013.01)

(58) Field of Classification Search
CPC .................................................. C12N 9/1252
See application file for complete search history.

(56) References Cited

U.S. PATENT DOCUMENTS

| 6,008,025 | A | 12/1999 | Komatsubara et al. | |
| 6,946,273 | B1 | 9/2005 | Sorge et al. | |
| 7,384,739 | B2* | 6/2008 | Kitabayashi | C07K 14/195 435/183 |
| 8,283,148 | B2* | 10/2012 | Sorge | C07H 21/04 435/194 |
| 8,557,554 | B2* | 10/2013 | Connolly | C12N 9/1252 435/183 |
| 2002/0076768 | A1 | 6/2002 | Kuroita et al. | |
| 2004/0081965 | A1 | 4/2004 | Sorge et al. | |
| 2005/0069908 | A1* | 3/2005 | Sorge | C07H 21/04 435/6.11 |
| 2006/0057682 | A1* | 3/2006 | Connolly | C12N 9/1252 435/91.2 |

FOREIGN PATENT DOCUMENTS

| JP | 10-42872 A | 2/1998 |
| JP | 2002-253265 A | 9/2002 |
| JP | 2005-526510 A | 9/2005 |
| JP | 2006-507012 A | 3/2006 |
| JP | 2006-513726 A | 4/2006 |
| JP | 2006-521112 A | 9/2006 |
| JP | 2010-35533 A | 2/2010 |
| JP | 2010-505410 A | 2/2010 |
| WO | 03/089637 A1 | 10/2003 |
| WO | 2004/038007 A2 | 5/2004 |
| WO | 2004/058942 A2 | 7/2004 |
| WO | 2004/087868 A2 | 10/2004 |
| WO | 2008/041825 A1 | 4/2008 |
| WO | 2012/154934 A1 | 11/2012 |

OTHER PUBLICATIONS

Morrison. Nucleotide sequence of the POL3 gene encoding DNA polymerase III (delta) of *Saccharomyces cerevisiae*. Nucleic Acids Res. Jan. 25, 1992;20(2):375.*
Branden et al. Introduction to Protein Structure, Garland Publishing Inc., New York, p. 247, 1991.*
Tubeleviciute et al., "Compartmentalized self-replication (CSR) selection of Thermococcus litoralis Sh I B DNA polymerase for diminished uracil binding", Protein Engineering, Design & Selection, vol. 23, No. 8, 2010, pp. 589-597; cited in the ISR.
Firbank et al., "Uracil Recognition in Archaeal DNA Polymerases Captured by X-ray Crystallography", Journal of Molecular Biology, vol. 381(3), 2008, pp. 529-539.
Longo et al., "Use of uracil DNA glycosylase to control carry-over contamination in polymerase chain reactions", Gene, vol. 93(1), 1990, pp. 125-128.
Sakaguchi et al., "Cautionary Note on the Use of dUMP-Containing PCR Primers with Pfu and VentR® DNA Polymerases", BioTechniques, vol. 21, No. 3, Sep. 1996, pp. 368-370.
Slupphaug et al., "Low Incorporation of dUMP by Some Thermostable DNA Polymerases May Limit Their Use in PCR Amplifications", Analytical Biochemistry, vol. 211(1), 1993, pp. 164-169.
Hogrefe et al., "Archeal dUTPase enhances PCR amplifications with archaeal DNA polymerases by preventing dUTP incorporation", Proceedings of the National Academy of Sciences of the United States of America, vol. 99, No. 2, Jan. 22, 2002, pp. 596-601.

(Continued)

*Primary Examiner* — Yong D Pak
(74) *Attorney, Agent, or Firm* — Westerman, Hattori, Daniels & Adrian, LLP

(57) ABSTRACT

A modified DNA, polymerase belonging to family B that is not inhibited by dUTP is provided.
The modified DNA polymerase comprises modifications of at least two amino acids selected from the group consisting of amino acids corresponding to Y7, P36, and V93 in SEQ ID NO: 1, in the amino acid sequence represented by any one of SEQ ID NOs: 1 to 10.

16 Claims, 12 Drawing Sheets

(56) References Cited

OTHER PUBLICATIONS

Choi et al., "Unique Substrate Spectrum and PCR Application of Nanoarchaeum equitans Family B DNA Polymerase", Applied and Environmental Microbiology, vol. 74, No. 21, Nov. 2008, pp. 6563-6569.

Fogg et al., "Structural basis for uracil recognition by archaeal family B DNA polymerases", Nature Structural Biology, vol. 9, No. 12, Dec. 2002, pp. 922-927.

International Search Report dated Nov. 12, 2013 issued in corresponding application PCT/JP2013/076217.

Extended (supplementary) European Search Report dated Apr. 12, 2016, issued in counterpart European Patent Application No. 13841851.2. (6 pages).

\* cited by examiner

Fig. 1

| | | |
|---|---|---|
| SEQ ID NO: 1 | 1 | MILDTDYITEDGKPVIRIFKKENGEFKIEYDRTFEPYFYALLKDDSAIEEVKKITAERHG 60 |
| SEQ ID NO: 2 | 1 | MILDVDYITEEGKPVIRLFKKENGKFKIEHDRTFRPYIYALLRDDSKIEEVKKITGERHG 60 |
| SEQ ID NO: 3 | 1 | MILDTDYITEDGKPVIRIFKKENGEFKIDYDRNFEPYIYALLKDDSAIEDVKKITAERHG 60 |
| SEQ ID NO: 4 | 1 | MILDTDYITKDGKPIIRIFKKENGEFKIELDPHFQPYIYALLKDDSAIEEIKAIKGERHG 60 |
| SEQ ID NO: 5 | 1 | MILDADYITEDGKPIIRIFKKENGEFKVEYDRNFRPYIYALLKDDSQIDEVRKITAERHG 60 |
| SEQ ID NO: 6 | 1 | MILDVDYITENGKPVIRVFKKENGEFRIEYDREFEPYFYALLRDDSAIEEIKKITAERHG 60 |
| SEQ ID NO: 7 | 1 | MILDTDYITENGKPVIRVFKKENGEFKIEYDRTFEPYFYALLKDDSAIEDVKKVTAKRHG 60 |
| SEQ ID NO: 8 | 1 | MILDTDYITENGKPVIRIFKKENGEFKIEYDRTFEPYIYALLKDDSAIEEVKKITAERHG 60 |
| SEQ ID NO: 9 | 1 | MILDADYITEDGKPVVRIFRKEKGEFRIDYDRDFEPYIYALLKDDSAIEEVKRITVERHG 60 |
| SEQ ID NO:10 | 1 | MILDTDYITEDGKPVIRIFKKENGEFKIEYDRTFEPYIYALLKDDSAIEDVKKITAERHG 60 |

| | | |
|---|---|---|
| SEQ ID NO: 1 | 61 | TVVTVKRVEKVQKKFLGRPVEVWKLYFTHPQDVPAIRDKIREHPAVIDIYEYDIPFAKRY 120 |
| SEQ ID NO: 2 | 61 | KIVRIVDVEKVEKKFLGKPITVWKLYLEHPQDVPTIREKVREHPAVVDIFEYDIPFAKRY 120 |
| SEQ ID NO: 3 | 61 | TTVRVVRAEKVKKKFLGRPIEVWKLYFTHPQDVPAIRDKIKEHPAVVDIYEYDIPFAKRY 120 |
| SEQ ID NO: 4 | 61 | KTVRVLDAVKVRKKFLGREVEVWKLIFEHPQDVPAMRGKIREHPAVVDIYEYDIPFAKRY 120 |
| SEQ ID NO: 5 | 61 | KIVRIIDAEKVRKKFLGRPIEVWRLYFEHPQDVPAIRDKIREHSAVIDIFEYDIPFAKRY 120 |
| SEQ ID NO: 6 | 61 | RVVKVKRAEKVKKKFLGRSVEVWVLYFTHPQDVPAIRDKIRKHPAVIDIYEYDIPFAKRY 120 |
| SEQ ID NO: 7 | 61 | TVVKVKRAEKVQKKFLGRPIEVWKLYFNHPQDVPAIRDRIRAHPAVVDIYEYDIPFAKRY 120 |
| SEQ ID NO: 8 | 61 | TVVTVKRAEKVQKKFLGRPVEVWKLYFTHPQDVPAIRDKIREHPAVIDIYEYDIPFAKRY 120 |
| SEQ ID NO: 9 | 61 | KAVRVKRVEKVEKKFLNRPIEVWKLYFNHPQDVPAIRDEIRKHPAVVDIYEYDIPFAKRY 120 |
| SEQ ID NO:10 | 61 | TVVKVKRAEKVQKKFLGRPVEVWKLYFTHPQDVPAIRDKIRKHPAVIDIYEYDIPFAKRY 120 |

| | | |
|---|---|---|
| SEQ ID NO: 1 | 121 | LIDKGLVPMEGDEELKMLAFDIETLYHEGEEFAEGPILMISYADEEGARVITWKNVDLPY 180 |
| SEQ ID NO: 2 | 121 | LIDKGLIPMEGEEELKILAFDIETLYHEGEEFGKGPIIMISYADENEAKVITWKNIDLPY 180 |
| SEQ ID NO: 3 | 121 | LIDKGLIPMEGDEELKMLAFDIETLYHEGEEFAEGPILMISYADEEGARVITWKNIDLPY 180 |
| SEQ ID NO: 4 | 121 | LIDKGLIPMEGDEELKLLAFDIETFYHEGDEFGKGEIIMISYADEEEARVITWKNIDLPY 180 |
| SEQ ID NO: 5 | 121 | LIDKGLIPMEGDEELKLLAFDIETLYHEGEEFAKGPIIMISYADEEEAKVITWKKIDLPY 180 |
| SEQ ID NO: 6 | 121 | LIDKGLIPMEGEEELKLMSFDIETLYHEGEEFGTGPILMISYADESEARVITWKKIDLPY 180 |
| SEQ ID NO: 7 | 121 | LIDKGLIPMEGDEELTMLAFDIETLYHEGEEFGTGPILMISYADGSEARVITWKKIDLPY 180 |
| SEQ ID NO: 8 | 121 | LIDKGLVPMEGDEELKMLAFDIETLYHEGEEFAEGPILMISYADEEGARVITWKNADLPY 180 |
| SEQ ID NO: 9 | 121 | LIDKGLVPMEGEEELKLMAFDIETLYHEGDEFGEGPILMISYADGDGARVITWKKIDLPY 180 |
| SEQ ID NO:10 | 121 | LIDKGLVPMEGEEELKMLAFDIETLYHEGEEFAEGPILMISYADESEARVITWKKIDLPY 180 |

Fig. 2

```
SEQ ID NO:  1  121:LIDKGLVPMEGDEELKMLAFDIETLYHEGEEFAEGPILMISYADEEGARVITWKNVDLPY 180
SEQ ID NO:  2  121:LIDKGLIPMEGEEELKILAFDIETLYHEGEEFGKGPIIMISYADENEAKVITWKNIDLPY 180
SEQ ID NO:  3  121:LIDKGLIPMEGDEELKMLAFDIETLYHEGEEFAEGPILMISYADEEGARVITWKNIDLPY 180
SEQ ID NO:  4  121:LIDKGLIPMEGDEELKLLAFDIETPYHEGDEFGKGEIIMISYADEEEARVITWKNIDLPY 180
SEQ ID NO:  5  121:LIDKGLIPMEGDEELKLLAFDIETLYHEGEEFAKGPIIMISYADEEEAKVITWKKIDLPY 180
SEQ ID NO:  6  121:LIDKGLIPMEGEEELKLMSFDIETLYHEGEEFGTGPLMISYADESEARVITWKKIDLPY 180
SEQ ID NO:  7  121:LIDKGLIPMEGDEELTMLAFDIETLYHEGEEFGTGPLMISYADGSEARVITWKKIDLPY 180
SEQ ID NO:  8  121:LIDKGLVPMEGDEELKMLAFDIETLYHEGEEFAEGPILMISYADEEGARVITWKNADLPY 180
SEQ ID NO:  9  121:LIDKGLVPMEGEEELKLMAFDIETLYHEGDEFGEGPILMISYADGDGARVITWKKIDLPY 180
SEQ ID NO:10  121:LIDKGLIPMEGEEELKMLAFDIETLYHEGEEFAEGPILMISYADESEARVITWKKIDLPY 180
                  ******.****.***.  *****.****.**   *.*.******. .*.***** .****

SEQ ID NO:  1  181:VDVVSTEREMIKRFLRVVKEKDPDVLITYNGDNFDFAYLKKRCEKLGINFALGRDGSE-- 238
SEQ ID NO:  2  181:VEVVSSEREMIKRFLRIIREKDPDIIVTYNGDSFDFPYLAKRAEKLGIKLTIGRDCGSE-- 238
SEQ ID NO:  3  181:VDVVSTEKEMIKRFLKVVKEKDPDVLITYNGDNFDFAYLKKRSEKLGVKFILGREGSE-- 238
SEQ ID NO:  4  181:VDVVSNEREMIKRFVQVVKEKDPDVIITYNGDNFDLPYLIKRAEKLGVRLVLGRDKEHPE 240
SEQ ID NO:  5  181:VEVVSSEREMIKRFLKVIREKDPDVIITYNGDSFDLPYLVKRAEKLGIKLPLGRDGSE-- 238
SEQ ID NO:  6  181:VEVVSTEKEMIKRFLRVVKEKDPDVLITYNGDNFDFAYLKKRCEKLGVSFTLGRDGSE-- 238
SEQ ID NO:  7  181:VDVVSTEKEMIKRFLRVVKEKDPDVLITYNGDNFDFAYLKKRCEELGIKFTLGRDGSE-- 238
SEQ ID NO:  8  181:VDVVSTEREMIKRFLKVVKEKDPDVLITYNGDNFDFAYLKKRCEKLGINFTLGRDGSE-- 238
SEQ ID NO:  9  181:VDVVSTEKEMIKRFLQVVKEKDPDVLVTYNGDNFDFAYLKRRSEELGLKFILGRDGSE-- 238
SEQ ID NO:10  181:VDVVSTEKEMIKRFLRVVKEKDPDVLITYNGDNFDFAYLKKRCEKLGINFLLGRDGSE-- 238
                  *.***.* ******.   *****. *****.**  **.*  *.**. . .**....

SEQ ID NO:  1  239:PKIQRMGDRFAVEVKGRIHFDLYPVIRRTINLPTYTLEAVYEAVFGQPKEKVYAEEITTA 298
SEQ ID NO:  2  239:PKMQRIGDMTAVEVKGRIHFDLYHVITRTINLPTYTLEAVYEAIFGKPKEKVYADEIAKA 298
SEQ ID NO:  3  239:PKIQRMGDRFAVEVKGRIHFDLYPVIRRTINLPTYTLEAVYEAIFGQPKEKVYAEEIAQA 298
SEQ ID NO:  4  241:PKIQRMGDSFAVEIKGRIHFDLFPVVRRTINLPTYTLEAVYEAVLGKTKSKLGAEEIAAI 300
SEQ ID NO:  5  239:PKMQRLGDMTAVEIKGRIHFDLYHVIRRTINLPTYTLEAVYEAIFGKPKEKVYAHEIAEA 298
SEQ ID NO:  6  239:PKIQRMGDRFAVEVKGRVHFDLYPVIRRTINLPTYTLEAVYEAVFGKPKEKVYAEEIATA 298
SEQ ID NO:  7  239:PKIQRMGDRFAVEVKGRIHFDLYPVIRRTINLPTYTLEAVYEAVFGKPKEKVYAEEIAQA 298
SEQ ID NO:  8  239:PKIQRMGDRFAVEVKGRIHFDLYPVIRRTINLPTYTLEAVYEAVFGQPKEKVYAEEIATA 298
SEQ ID NO:  9  239:PKIQRMGDRFAVEVKGRIHFDLYPVIRRTVNLPTYTLEAVYEAIFGRPKEKVYAGEIVEA 298
SEQ ID NO:10  239:PKIQRMGDRFAVEVKGRIHFDLYPVIRRTINLPTYMLEAVYEAIFGKPKEKVYAEEIATA 298
                  **.**.**..***.***.****..*..**.*****.*******  .*..*.*..*.**. .

SEQ ID NO:  1  299:WETGENLERVARYSMEDAKVTYELGKEFLPMEAQLSRLIGQSLWDVSRSSTGNLVEWFLL 358
SEQ ID NO:  2  299:WESGENLERVAKYSMEDAKATYELGKEFLPMEIQLSRLVGQPLWDVSRSSTGNLVEWFLL 358
SEQ ID NO:  3  299:WETGEGLERVARYSMEDAKVTYELGKEFFPMEAQLSRLVGQSLWDVSRSSTGNLVEWFLL 358
SEQ ID NO:  4  301:WETEESMKKLAQYSMEDARATYELGKEFFPMEAELAKLIGQSVWDVSRSSTGNLVEWYLL 360
SEQ ID NO:  5  299:WETGKGLERVAKYSMEDARVTYELGREFFPMEAQLSRLVGQPLWDVSRSSTGNLVEWYLL 358
SEQ ID NO:  6  299:WETGEGLERVARYSMEDARVTYELGREFFPMEAQLSRLIGQGLWDVSRSSTGNLVEWFLL 358
SEQ ID NO:  7  299:WESGEGLERVARYSMEDAKVTYELGKEFFPMEAQLSRLIGQSLWDVSRSSTGNLVEWFLL 358
SEQ ID NO:  8  299:WESGEGLERVARYSMEDAKVTYELGKEFFPMEAQLSRLIGQSLWDVSRSSTGNLVEWFLL 358
SEQ ID NO:  9  299:WETGEGLERVARYSMEDAKVTFELGKEFFPMEAQLSRLIGQGLWDVSRSSTGNLVEWFLL 358
SEQ ID NO:10  299:WETGEGLERVARYSMEDAKVTFELGKEFFPMEAQLSRLVGQSFWDVARSSTGNLVEWFLL 358
                  **........*.******.*.***.**.***..*..*.**...***.**********.**
```

1: 75pmol Primer
2: 150pmol Primer

1 Fwd: AAGAGAGGGTTGGAGAGTAG           SEQ ID NO: 42
  Rev: CCCCTAAAAAAAAAATCAAAAATC       SEQ ID NO: 43
2 Fwd: GAGTTGGTGATGTTAGATTAG          SEQ ID NO: 44
  Rev: TTCCCAAAAAAATCCCAAATTC         SEQ ID NO: 45
3 Fwd: AGAGAGGAGTTTAGATTGG             SEQ ID NO: 46
  Rev: CAAAAAAACTAAAACCTCAAC          SEQ ID NO: 47
4 Fwd: TTTATTTATATAATTTTGTGTATGG      SEQ ID NO: 48
  Rev: CACCCCTCACTTTACTAAAAC          SEQ ID NO: 49

1: 0.5U
2: 0.25U
3: 0.125U
4: 0.063U
5: 0.032U
6: No UNG

MODIFIED DNA POLYMERASE

TECHNICAL FIELD

The present invention relates to a modified DNA polymerase for use in polymerase chain reaction (PCR) and the like, and a method for producing the same. The present invention further relates to a nucleic acid amplification method using the modified DNA polymerase, and a reagent comprising the modified DNA polymerase. The present invention can be used not only for research, but also clinical diagnosis, environmental testing, etc.

BACKGROUND ART

Thermostable DNA polymerases used for PCR are those belonging to family A and those belonging to family B. Examples of known DNA polymerases belonging to family A include DNA polymerase derived from *Thermus thermophilus* (Tth polymerase), DNA polymerase derived from *Thermus aquaticus* (Taq polymerase), and the like. Examples of known DNA polymerases belonging to family B include DNA polymerase derived from *Pyrococcus furiosus* (Pfu polymerase), thermostable DNA polymerase derived from *Thermococcus litoralis* (Tli polymerase), DNA polymerase derived from *Thermococcus kodakaraensis* (KOD DNA polymerase), and the like.

DNA polymerases belonging to family A have been heretofore used as thermostable DNA polymerases used for PCR for reasons such as good amplification efficiency and easy condition setting. However, recent various investigations into reaction compositions etc. have enabled easy condition setting even with DNA polymerases belonging to family B. In addition, DNA polymerases belonging to family B have high fidelity and thermostability, and are resistant to inhibiting substances carried into the reaction system; therefore, DNA polymerases belonging to family B have been widely used not only in the research field, but also in the field of forensic medicine, such as in genetic diagnosis and clinical diagnosis. DNA polymerases belonging to family B have also been widely used in testing for microorganisms in foods and the environment, etc.

DNA polymerases belonging to family B are, however, problematic in that when dUTP is incorporated, reactions stop because of their high fidelity. Since dUTP is also generated by thermal decomposition of dCTP, DNA polymerases belonging to family B are affected by dUTP generated during thermal cycling of PCR, and thus cannot sufficiently exhibit their high amplification efficiency. In particular, DNA polymerases belonging to family B are known to have reduced amplification efficiency in PCR using a long-chain target as a template, which requires a long thermal cycling time, and in PCR performed at multiple cycles using a small amount of template.

Additionally, since PCR is a highly sensitive detection method, carryover of amplification products from previous PCR may lead to false-positive results. To address this problem, a technique is taken in which PCR is performed using substrates containing dUTP instead of dTTP to incorporate uracil bases into amplification products, and contamination (carryover) PCR amplification products are degraded by treating with uracil-N-glycosylase (UNG) when the next PCR is performed (dUTP/UNG decontamination method) (Non-patent Literature 1). Although DNA polymerases belonging to family B have advantages of high fidelity and thermostability as well as resistance to inhibiting substances carried into the reaction system, they cannot be used in such a technique, since dUTP cannot be incorporated (Non-patent Literature 2, Non-patent Literature 3, and Non-patent Literature 4).

In recent years, interaction of DNA polymerases belonging to family B with nucleic acid containing dUTP has been studied, and an analysis of crystal structure of DNA polymerase derived from *Thermococcus gorgonarius* (Tgo polymerase) with dUTP was carried out. The results of the analysis suggest the presence of uracil binding pockets that are formed by amino acids at positions 1 to 40 and amino acids at positions 78 to 130 in Tgo polymerase, and show that strong interaction of one of the uracil binding pockets with dUTP shops extension reactions of PCR (Non-patent Literature 5).

It was then found that DNA polymerases in which an amino acid associated with uracil binding pockets is modified have reduced affinity for dUTP, thus allowing PCR to be performed even in the presence of dUTP. However, it has been impossible for even these DNA polymerases, in which an amino acid associated with uracil binding pockets is modified, to provide sufficient amounts of PCR amplification and to fully exhibit amplification efficiency of DNA polymerases belonging to family B. In addition, since reduction in enzyme activity has been expected, multiple mutations in amino acids associated with uracil binding pockets have not heretofore been considered (Patent Literature 1 and 2).

CITATION LIST

Patent Literature

PTL 1: JP2005-526510A
PTL 2: JP2006-507012A
PTL 3: U.S. Pat. No. 6,946,273

Non-Patent Literature

NPL 1: Gene, Vol. 93 (1), 125-128 (1990)
NPL 2: BioTechniques, Vol. 21 (3), 368-370 (1996)
NPL 3: Analytical Biochemistry, Vol. 211 (1), 164-169 (1993)
NPL 4: Proceedings of the National Academy of Sciences of the United States of America, Vol. 99, 596-601 (2002)
NPL 5: Journal of Molecular Biology, Vol. 381 (3), 529-539 (2008)

SUMMARY OF INVENTION

Technical Problem

As described above, DNA polymerases belonging to family B are widely used not only in the research field, but also in the field of forensic medicine, such as in genetic diagnosis and clinical diagnosis; DNA polymerases belonging to family B are also widely used in testing for microorganisms in foods and the environment, etc. However, dUTP/UNG decontamination methods cannot be used with such polymerases, since PCR reactions are stopped by the presence of dUTP. Additionally, dUTP generated by thermal decomposition of dCTP during thermal cycling prevents DNA polymerases belonging to family B from sufficiently exhibiting their amplification efficiency. Therefore, an object of the present invention is to provide a modified DNA polymerase belonging to family B that is not inhibited by dUTP.

Solution to Problem

The present inventors found that in a DNA polymerase derived from the genus *Pyrococcus* or the genus *Thermococcus*, sensitivity to uracil is notably reduced when one or more specific amino acids in the amino acid sequences involved in uracil binding are modified. The present inventors conducted further examination and investigation based on this finding, and accomplished the present invention.

The present invention provides the following representative modified DNA polymerase, a nucleic acid amplification method using the modified DNA polymerase, and a reagent for nucleic acid amplification, the reagent comprising the modified DNA polymerase.

Item A1. A modified DNA polymerase comprising modifications of at least two amino acids selected from the group consisting of amino acids corresponding to Y7, P36, and V93 in SEQ ID NO: 1, in the amino acid sequence represented by any one of SEQ ID NOs: 1 to 10.

Item A2. The modified DNA polymerase according to Item A1, comprising at least two amino acid substitutions selected from (a) to (c) below:
(a) Y7A,
(b) P36H, P36R, or P36K, and
(c) V93K, V93Q, V93R, or V93H.

Item A3. The modified DNA polymerase according to Item A1 or A2, further comprising a modification of at least one amino acid selected from the group consisting of amino acids corresponding to D141, I142, E143, H147, and N210 in SEQ ID NO: 1.

Item A4. The modified DNA polymerase according to Item A3, comprising at least one amino acid substitution selected from (d) to (g) below:
(d) D141A and E143A,
(e) I142R,
(f) N210D, and
(g) H147E or H147D.

Item A5. A method for amplifying nucleic acids, comprising using the modified DNA polymerase according to any one of Items A1 to A4.

Item A6. The method according to Item A5, comprising using inosine-containing primers.

Item A7. The method according to Item A5, comprising using bisulfite-treated DNA as a template.

Item A8. A dUTP/UNG decontamination method comprising degrading, with uracil-DNA glycosylase, nucleic acids amplified by the method according to Item A5.

Item A9. A reagent for amplifying nucleic acids, comprising the modified DNA polymerase according to any one of Items A1 to A4.

Item A10. A kit comprising the reagent according to Item A9.

Item A11. A modified DNA polymerase comprising a modification of an amino acid corresponding to P36 in SEQ ID NO: 1, in the amino acid sequence represented by any one of SEQ ID NOs: 1 to 3 and 5 to 10.

Item A12. The modified DNA polymerase according to Item A11, comprising a P36H, P36R, or P36K amino acid substitution.

Item A13. The modified DNA polymerase according to Item A11 or A12, further comprising a modification of at least one amino acid selected from the group consisting of amino acids corresponding to D141, I142, E143, H147, and N210 in SEQ ID NO: 1.

Item A14. The modified DNA polymerase according to Item A13, comprising at least one amino acid substitution selected from (h) to (k) below:
(h) D141A and E143A,
(i) I142R,
(j) N210D, and
(k) H147E or H147D.

Item A15. A method for amplifying nucleic acids, comprising using the modified DNA polymerase according to any one of Items A11 to A14.

Item A16. The method according to Item A15 comprising using inosine-containing primers.

Item A17. The method according to Item A15, comprising using bisulfite-treated DNA as a template.

Item A18. A dUTP/UNG decontamination method comprising degrading, with uracil-DNA glycosylase, nucleic acids amplified by the method according to Item A15.

Item A19. A reagent for amplifying nucleic acids, comprising the modified polymerase according to any one of Items A11 to A14.

Item A20. A kit comprising the reagent according to Item A19.

Item B1. A modified DNA polymerase comprising at least two amino acid modifications in amino acid sequences involved in uracil binding, and having lower uracil sensitivity than that of a wild-type DNA polymerase, the modified DNA polymerase being derived from the genus *Pyrococcus* or the genus *Thermococcus*.

Item B2. The modified DNA polymerase according to Item B1, comprising modifications of at least two amino acids among amino acids corresponding to positions 7, 36, 37, 90 to 97, and 112 to 119 in the amino acid sequence represented by SEQ ID NO: 1, the amino acids being involved in uracil binding, the modified DNA polymerase having lower uracil sensitivity than that of a wild-type DNA polymerase.

Item B3. The modified DNA polymerase according to Item B2, comprising modifications of at least two amino acids among amino acids corresponding to Y7, P36, and V93 in the amino acid sequence represented by SEQ ID NO: 1, and having lower uracil sensitivity than that of a wild-type DNA polymerase.

Item B4. The modified DNA polymerase according to Item B3, wherein the modification of the amino acid corresponding to Y7 is an amino acid substitution selected from the group consisting of Y7A, Y7G, Y7V, Y7L, Y7I, Y7P, Y7F, Y7M, Y7W, and Y7C.

Item B5. The modified DNA polymerase according to Item B3 or B4, wherein the modification of the amino acid corresponding to P36 is a P36H, P36K, or P36R amino acid substitution.

Item B6. The modified DNA polymerase according to any one of Items B3 to B5, wherein the modification of the amino acid corresponding to V93 is a V93H, V93K, or V93R amino acid substitution.

Item B7. The modified DNA polymerase according to any one of Items B3 to B6, wherein the modifications of the at least two amino acids are Y7A and P36H amino acid substitutions.

Item B8. The modified DNA polymerase according to Item B3, wherein the modifications of the at least two amino acids are Y7A, and P36K amino acid substitutions.

Item B9. The modified DNA polymerase according to Item B3, wherein the modifications of the at least two amino acids are Y7A and P36R amino acid substitutions.

Item B10. The modified DNA polymerase according to Item B3, wherein the modifications of the at least two amino acids are Y7A and V93Q amino acid substitutions.

Item B11. The modified DNA polymerase according to Item B3, wherein the modifications of the at least two amino acids are Y7A and V93K amino acid substitutions.

Item B12. The modified DNA polymerase according to Item B3, wherein the modifications of the at least two amino acids are Y7A and V93R amino acid substitutions.

Item B13. The modified DNA polymerase according to Item B3, wherein the modifications of the at least two amino acids are P36H and V93K amino acid substitutions.

Item B14. The modified DNA polymerase according to any one of Items B1 to B13, further comprising at least one amino acid modification in amino acid sequences of 3'-5' exonuclease activity regions.

Item B15. The modified DNA polymerase according to Item B14, wherein the amino acid sequences of the 3'-5' exonuclease activity regions are amino acids corresponding to positions 137 to 147, 206 to 222, and 308 to 318 represented by SEQ ID NO: 1.

Item B16. The modified DNA polymerase according to Item B15, comprising a modification of at least one amino acid among amino acids corresponding to D141, I142, E143, H147, N210, and Y311 in the 3'-5' exonuclease activity regions.

Item B17. The modified DNA polymerase according to Item B16, wherein the modification in the amino acid sequences of the 3'-5' exonuclease activity regions is D141A and E143A.

Item B18. The modified DNA polymerase according to Item B16, wherein the modification in the amino acid sequences of the 3'-5' exonuclease activity regions is I142R.

Item B19. The modified DNA polymerase according to Item B16, wherein the modification in the amino acid sequences of the 3'-5' exonuclease activity regions is H147E or H147D.

Item B20. The modified DNA polymerase according to Item B16, wherein the modification in the amino acid sequences of the 3'-5' exonuclease activity regions is N210D.

Item B21. The modified DNA polymerase according to Item B16, wherein the modification in the amino acid sequences of the 3'-5' exonuclease activity regions is Y311F.

Item B22. The modified DNA polymerase according to any one of Items B1 to B21, wherein the DNA polymerase derived from the genus *Pyrococcus* or the genus *Thermococcus* is a DNA polymerase derived from *Pyrococcus furiosus, Pyrococcus* sp. GB-D, *Thermococcus kodakaraensis, Thermococcus gorgonarius, Thermococcus litoralis, Thermococcus* sp. JDF-3, *Thermococcus* sp. 9° N-7, *Thermococcus* sp. KS-1, *Thermococcus celer*, or *Thermococcus siculi*.

Item B23. The modified DNA polymerase according to any one of Items B1 to B22, wherein the wild-type DNA polymerase is a DNA polymerase that belongs to the genus *Pyrococcus* or the genus *Thermococcus*, and that comprises the amino acid sequence represented by any one of SEQ ID NOs: 1 to 10.

Item C1. A modified DNA polymerase comprising at least one amino acid modification in amino acid sequences involved in uracil binding and a modification of at least one amino acid among amino acids corresponding to I142, H147, N210, and Y311 in 3'-5' exonuclease activity regions, and having lower uracil sensitivity than that of a wild-type polymerase, the modified DNA polymerase being derived from the genus *Pyrococcus* or the genus *Thermococcus*.

Item C2. The modified DNA polymerase according to Item C1, comprising a modification of at least one amino acid among amino acids corresponding to Y7, P36, and V93 in the amino acid sequences involved in uracil binding.

Item C3. The modified DNA, polymerase according to Item C2, wherein the modification of the amino acid corresponding to Y7 is an amino acid substitution selected from the group consisting of Y7A, Y7G, Y7V, Y7L, Y7I, Y7P, Y7F, Y7M, Y7W, and Y7C.

Item C4. The modified DNA polymerase according to Item C2 or C3, wherein the modification of the amino acid corresponding to P36 is a P36H, P36K, or P36R amino acid substitution.

Item C5. The modified DNA polymerase according to any one of Items C2 to C4, wherein the modification of the amino acid corresponding to V93 is a V93H, V93K, or V93R amino acid substitution.

Item C6. The modified DNA polymerase according to any one of Items C1 to C5, wherein the modification in the amino acid sequences involved in uracil binding is at least one among Y7A, P36H, P36K, P36R, V93Q, V93K, and V93R.

Item C7. The modified DNA polymerase according to any one of Items C1 to C6, wherein the modification of the amino acid corresponding to I142 is an I142R amino acid substitution.

Item C8. The modified DNA polymerase according to any one of Items C1 to C7, wherein the modification of the amino acid corresponding to H147 is an H147E or H147D amino acid substitution.

Item C9. The modified DNA polymerase according to any one of Items C1 to C8, wherein the modification of the amino acid corresponding to N210 is an N210D amino acid substitution.

Item C10. The modified DNA polymerase according to any one of Items C1 to C9, wherein the modification of the amino acid corresponding to Y311 is a Y311F amino acid substitution.

Item C11. The modified DNA polymerase according to any one of Items C1 to C10, wherein the DNA polymerase derived from the genus *Pyrococcus* or the genus *Thermococcus* is a DNA polymerase derived from *Pyrococcus furiosus, Pyrococcus* sp. GB-D, *Thermococcus kodakaraensis, Thermococcus gorgonarius, Thermococcus litoralis, Thermococcus* sp. JDF-3, *Thermococcus*sp. 9° N-7, *Thermococcus* sp. KS-1, *Thermococcus celer*, or *Thermococcus siculi*.

Item C12. The modified DNA polymerase according to any one of Items C1 to C11, wherein the wild-type polymerase is a DNA polymerase that belongs to the genus *Pyrococcus* or the genus *Thermococcus*, and that comprises the amino acid sequence represented by any one of SEQ ID NOs: 1 to 10.

Item D1. A modified DNA polymerase comprising at least one amino acid modification in amino acid sequences involved in uracil binding and a modification of at least one amino acid among amino acids corresponding to I142, N210, and Y311 in 3'-5' exonuclease activity regions, and having lower uracil sensitivity than that of a wild-type polymerase, the modified DNA polymerase being derived from the genus *Pyrococcus* or the genus *Thermococcus*.

Item D2. The modified DNA polymerase according to Item D1, comprising a modification of at least one amino acid among amino acids corresponding to Y7, P36, and V93 in the amino acid sequences involved in uracil binding.

Item D3. The modified DNA polymerase according to D2, wherein the modification of the amino acid corresponding to Y7 is an amino acid substitution selected from the group consisting of Y7A, Y7G, Y7V, Y7L, Y7I, Y7P, Y7F, Y7M, Y7W, and Y7C.

Item D4. The modified DNA polymerase according to Item D2 or D3, wherein the modification of the amino acid corresponding to P36 is a P36H, P36K, or P36R amino acid substitution.

Item D5. The modified DNA polymerase according to any one of Items D2 to D4, wherein the modification of the amino acid corresponding to V93 is a V93H, V93K, or V93R amino acid substitution.

Item D6. The modified DNA polymerase according to any one of Items D1 to D5, wherein the modification in the amino acid sequences involved in uracil binding is at least one among Y7A, P36H, P36K, P36R, V93Q, V93K, and V93R.

Item D7. The modified DNA polymerase according to any one of D1 to D6, wherein the modification of the amino acid corresponding to I142 is an I142R amino acid substitution.

Item D8. The modified DNA polymerase according to any one of Items D1 to D7, wherein the modification of the amino acid corresponding to N210 is an N210D amino acid substitution.

Item D9. The modified DNA polymerase according to any one of Items D1 to D8, wherein the modification of the amino acid corresponding to Y311 is a Y311F amino acid substitution.

Item D10. The modified DNA polymerase according to any one of Items D1 to D9, further comprising an H147E or H147D amino acid substitution.

Item D11. A modified DNA polymerase comprising a modification of at least one amino acid among Y7 and P36 in amino acid sequences involved in uracil binding and a modification of at least one amino acid among amino acids corresponding to D141 and E143 in 3'-5' exonuclease activity regions, and having lower uracil sensitivity than that of a wild-type polymerase, the modified DNA polymerase being derived from the genus *Pyrococcus* or the genus *Thermococcus*.

Item D12. The modified DNA polymerase according to Item D11, comprising a modification of at least one amino acid among amino acids corresponding to Y7, P36, and V93 in the amino acid sequences involved in uracil binding.

Item D13. The modified DNA polymerase according to Item D12, wherein the modification of the amino acid corresponding to Y7 is an amino acid substitution selected from the group consisting of Y7A, Y7G, Y7V, Y7L, Y7I, Y7P, Y7F, Y7M, Y7W, and Y7C.

Item D14. The modified DNA polymerase according to Item D12 or D13, wherein the modification of the amino acid corresponding to P36 is a P36H, P36K, or P36R amino acid substitution.

Item D15. The modified DNA polymerase according to any one of Items D12 to D14, wherein the modification of the amino acid corresponding to D141 is a D141A amino acid substitution.

Item D16. The modified DNA polymerase according to any one of Items D12 to D15, wherein the modification of the amino acid corresponding to E143 is an E143A amino acid substitution.

Item D17. The modified DNA polymerase according to any one of Items D12 to D16, further comprising an H147E or H147D amino acid substitution.

Item D18. The modified DNA polymerase according to any one of Items D1 to D17, wherein the DNA polymerase derived from the genus *Pyrococcus* or the genus *Thermococcus* is a DNA polymerase derived from *Pyrococcus furiosus*, *Pyrococcus* sp. GB-D, *Thermococcus kodakaraensis*, *Thermococcus gorgonarius*, *Thermococcus litoralis*, *Thermococcus* sp. JDF-3, *Thermococcus* sp. 9° N-7, *Thermococcus* sp. KS-1, *Thermococcus celer*, or *Thermococcus siculi*.

Item D19. The modified DNA polymerase according to any one of Items D1 to D18, wherein the wild-type polymerase is a DNA polymerase that belongs to the genus *Pyrococcus* or the genus *Thermococcus*, and that comprises the amino acid sequence represented by any one of SEQ ID NOs: 1 to 10.

Item D20. A method for performing a nucleic acid amplification reaction using the polymerase according to any one of Items D1 to D19.

Item D21. A method for performing a nucleic acid amplification reaction using the polymerase according to any one of Items D1 to D19 and inosine-containing primers.

Item D22. A method for performing a nucleic acid amplification reaction using the polymerase according to any one of Items D1 to D19 and bisulfite-treated DNA.

Item D23. A method for degrading nucleic acids amplified with the polymerase according to any one of Items D1 to D19, using uracil-DNA glycosylase.

Item D24. A reagent for performing a nucleic acid amplification reaction, comprising the polymerase according to any one of Items D1 to D19.

Item D25. A kit comprising a reagent for performing a nucleic acid amplification reaction and the polymerase according to any one of Items D1 to D19.

Item E1. A modified DNA polymerase comprising at least two amino acid modifications in amino acid sequences involved in uracil binding, and having lower uracil sensitivity than that of a wild-type DNA polymerase, the modified DNA polymerase being derived from the genus *Pyrococcus* or the genus *Thermococcus*.

Item E2. The modified DNA polymerase according to E1, comprising modifications of at least two amino acids among amino acids corresponding to positions 7, 36, 37, 90 to 97, and 112 to 119 in the amino acid sequence represented by SEQ ID NO: 1, the amino acids being involved in uracil binding, the modified DNA polymerase having lower uracil sensitivity than that of a wild-type DNA polymerase.

Item E3. The modified DNA polymerase according to Item E2, comprising modifications of at least two amino acids among amino acids corresponding to Y7, P36, and V93 in the amino acid sequence represented by SEQ ID NO: 1, and having lower uracil sensitivity than that of a wild-type DNA polymerase.

Item E4. The modified DNA polymerase according to Item E3, wherein the modification of the amino acid corresponding to Y7 is an amino acid substitution selected from the group consisting of Y7A, Y7G, Y7V, Y7L, Y7I, Y7P, Y7F, Y7M, Y7W, and Y7C.

Item E5. The modified DNA polymerase according to Item E3 or E4, wherein the modification of the amino acid corresponding to P36 is a P36H, P36K, or P36R amino acid substitution.

Item E6. The modified DNA polymerase according to any one of Items E3 to E5, wherein the modification of the amino acid corresponding to V93 is a V93H, V93K, or V93R amino acid substitution.

Item E7. The modified DNA polymerase according to any one of Items E3 to E6, wherein the modifications of the at least two amino acids are Y7A and P36H amino acid substitutions.

Item E8. The modified DNA polymerase according to Item E3, wherein the modifications of the at least two amino acids are Y7A and P36K amino acid substitutions.

Item E9. The modified DNA polymerase according to Item E3, wherein the modifications of the at least two amino acids are Y7A and P36R amino acid substitutions.

Item E10. The modified DNA polymerase according to Item E3, wherein the modifications of the at least two amino acids are Y7A and V93Q amino acid substitutions.

Item E11. The modified DNA polymerase according to Item E3, wherein the modifications of the at least two amino acids are Y7A and V93K amino acid substitutions.

Item E12. The modified DNA polymerase according to Item E3, wherein the modifications of the at least two amino acids are Y7A and V93R amino acid substitutions.

Item E13. The modified DNA polymerase according to Item E3, wherein the modifications of the at least two amino acids are P36H and V93K amino acid substitutions.

Item E14. The modified DNA polymerase according to any one of Items E1 to E13, further comprising at least one amino acid modification in amino acid sequences of 3'-5' exonuclease activity regions.

Item E15. The modified DNA polymerase according to Item E14, wherein the amino acid sequences of the 3'-5' exonuclease activity regions are amino acids corresponding to positions 137 to 147, 206 to 222, and 308 to 318 represented by SEQ ID NO: 1.

Item E16. The modified DNA polymerase according to Item E15, comprising a modification of at least one amino acid among amino acids corresponding to D141, I142, E143, H147, N210, and Y311 in the 3'-5' exonuclease activity regions.

Item E17. The modified DNA polymerase according to Item E16, wherein the modification in the amino acid sequences of the 3'-5' exonuclease activity regions is D141A and E143A.

Item E18. The modified DNA polymerase according to Item E16, wherein the modification in the amino acid sequences of the 3'-5' exonuclease activity regions is I142R.

Item E19. The modified DNA polymerase according to Item E16, wherein the modification in the amino acid sequences of the 3'-5' exonuclease activity regions is N210D.

Item E20. The modified DNA polymerase according to Item E16, wherein the modification in the amino acid sequences of the 3'-5' exonuclease activity regions is Y311F.

Item E21. The modified DNA polymerase according to any one of Items E1 to E20, further comprising an H247E or H147D amino acid substitution.

Item E22. The modified DNA polymerase according to any one of Items E1 to E21, wherein the DNA polymerase derived from the genus *Pyrococcus* or the genus *Thermococcus* is a DNA polymerase derived from *Pyrococcus furiosus, Pyrococcus* sp. GB-D, *Thermococcus kodakaraensis, Thermococcus gorgonarius, Thermococcus litoralis, Thermococcus* sp. JDF-3, *Thermococcus* sp. 9° N-7, *Thermococcus* sp. KS-1, *Thermococcus celer*, or *Thermococcus siculi*.

Item E23. The modified DNA polymerase according to any one of Items E1 to E22, wherein the wild-type DNA polymerase is a DNA polymerase that belongs to the genus *Pyrococcus* or the genus *Thermococcus*, and that comprises the amino acid sequence represented by any one of SEQ ID NOs: 1 to 10.

Item E24. A method for performing a nucleic acid amplification reaction using the polymerase according to any one of Items E1 to E23.

Item E25. A method for performing a nucleic acid amplification reaction using the polymerase according to any one of Items E1 to E23 and inosine-containing primers.

Item E26. A method for performing a nucleic acid amplification reaction using the polymerase according to any one of Items E1 to E23 and bisulfite-treated DNA.

Item E27. A method for degrading nucleic acids amplified with the polymerase according to any one of Items E1 to E23, using uracil-DNA glycosylase.

Item E28. A reagent for performing a nucleic acid amplification reaction, comprising the polymerase according to any one of Items E1 to E23.

Item E29. A kit comprising a reagent for performing a nucleic acid amplification reaction and the polymerase according to any one of Items E1 to E23.

Item F1. A modified DNA polymerase comprising a modification of an amino acid corresponding to P36 in amino acid sequences involved in uracil binding, and having lower uracil sensitivity than that of a wild-type polymerase, the modified DNA polymerase being derived from the genus *Pyrococcus* or the genus *Thermococcus*.

Item F2. The modified DNA polymerase according to Item F1, wherein the modification of the amino acid corresponding to P36 is a P36H amino acid substitution.

Item F3. The modified DNA polymerase according to Item F1, wherein the modification of the amino acid corresponding to P36 is a P36K amino acid substitution.

Item F4. The modified DNA polymerase according to Item F1, wherein the modification of the amino acid corresponding to P36 is a P36R amino acid substitution.

Item F5. The modified DNA polymerase according to any one of Items F1 to F4, further comprising a modification of an amino acid corresponding to Y7 or V93.

Item F6. The modified DNA polymerase according to Item F5, wherein the modification of the amino acid corresponding to Y7 is an amino acid substitution selected from the group consisting of Y7A, Y7G, Y7V, Y7L, Y7I, Y7P, Y7F, Y7M, Y7W, and Y7C.

Item F7. The modified DNA polymerase according to Item F5, wherein the modification of the amino acid corresponding to V93 is a V93H, V93K, or V93R amino acid substitution.

Item F8. The modified DNA polymerase according to any one of Items F1 to F7, further comprising D141A and E143A amino acid substitutions.

Item F9. The modified DNA polymerase according to any one of Items F1 to F8, further comprising an I142R amino acid substitution.

Item F10. The modified DNA polymerase according to any one of Items F1 to F9, further comprising a N210D amino acid substitution.

Item F11. The modified DNA polymerase according to any one of Items F1 to F10, further comprising an H147E or H147D amino acid substitution.

Item F12. The modified DNA polymerase according to any one of Items F1 to F11, wherein the DNA polymerase derived from the genus *Pyrococcus* or the genus *Thermococcus* is a DNA polymerase derived from *Pyrococcus furiosus, Pyrococcus* sp. GB-D, *Thermococcus kodakaraensis, Thermococcus gorgonarius, Thermococcus litoralis, Thermococcus* sp. JDF-3, *Thermococcus* sp. 9° N-7, *Thermococcus* sp. KS-1, *Thermococcus celer*, or *Thermococcus siculi*.

Item F13. The modified DNA polymerase according to any one of Items F1 to F12, wherein the wild-type polymerase is a DNA polymerase that belongs to the genus

*Pyrococcus* or the genus *Thermococcus*, and that comprises the amino acid sequence represented by any one of SEQ ID NOs: 1 to 10.

Item F14. A method for performing a nucleic acid amplification reaction using the polymerase according to any one of Items F1 to F13.

Item F15. A method for performing a nucleic acid amplification reaction using the polymerase according to any one of Items F1 to F13 and inosine-containing primers.

Item F16. A method for performing a nucleic acid amplification reaction using the polymerase according to any one of Items F1 to F13 and bisulfite-treated DNA.

Item F17. A method for degrading nucleic acids amplified with the polymerase according to any one of Items E1 to F13, using uracil-DNA glycosylase.

Item F18. A reagent for performing a nucleic acid amplification reaction, comprising the polymerase according to any one of Items F1 to F13.

Item F19. A kit comprising a reagent for performing a nucleic acid amplification reaction and the polymerase according to any one of Items F1 to F13.

Advantageous Effects of Invention

The present invention can provide a DNA polymerase that is not inhibited by dUTP, and that also exhibits high amplification efficiency in PCR using a long-chain target as a template, which requires a long thermal cycling time, and in PCR performed at multiple cycles using a small amount of template. With the characteristics of DNA polymerases belonging to family B, which have advantages such as high fidelity and thermostability, as well as resistance to inhibiting substances carried into the reaction system, the present invention can be applied to detection systems of extremely high sensitivity. Because of its high sensitivity and high fidelity, the modified DNA polymerase of the present invention can also be applied to emulsion PCR, which performs amplification from single molecules, bridge PCR, and next-generation sequencing techniques performed based on these techniques. In addition, the present invention allows the use of dUTP/UNG decontamination methods, which are methods to degrade contamination (carryover) amplification products; therefore, accurate results without false-positives can be obtained in diagnostic use, in which the same target is often amplified. Thus, the modified DNA polymerase of the present invention can be widely used in the research field, in the clinical or forensic medicine field, such as in genetic diagnosis, as well as in testing for microorganisms in foods and the environment, etc.

BRIEF DESCRIPTION OF DRAWINGS

FIG. 1 illustrates a comparison of amino acid regions involved in uracil binding in SEQ ID NOs: 1 to 10.

FIG. 2 illustrates a comparison of amino acid regions involved in 3'-5' exonuclease activity in SEQ ID NOs: 1 to 10.

DESCRIPTION OF EMBODIMENTS

Figure 3:
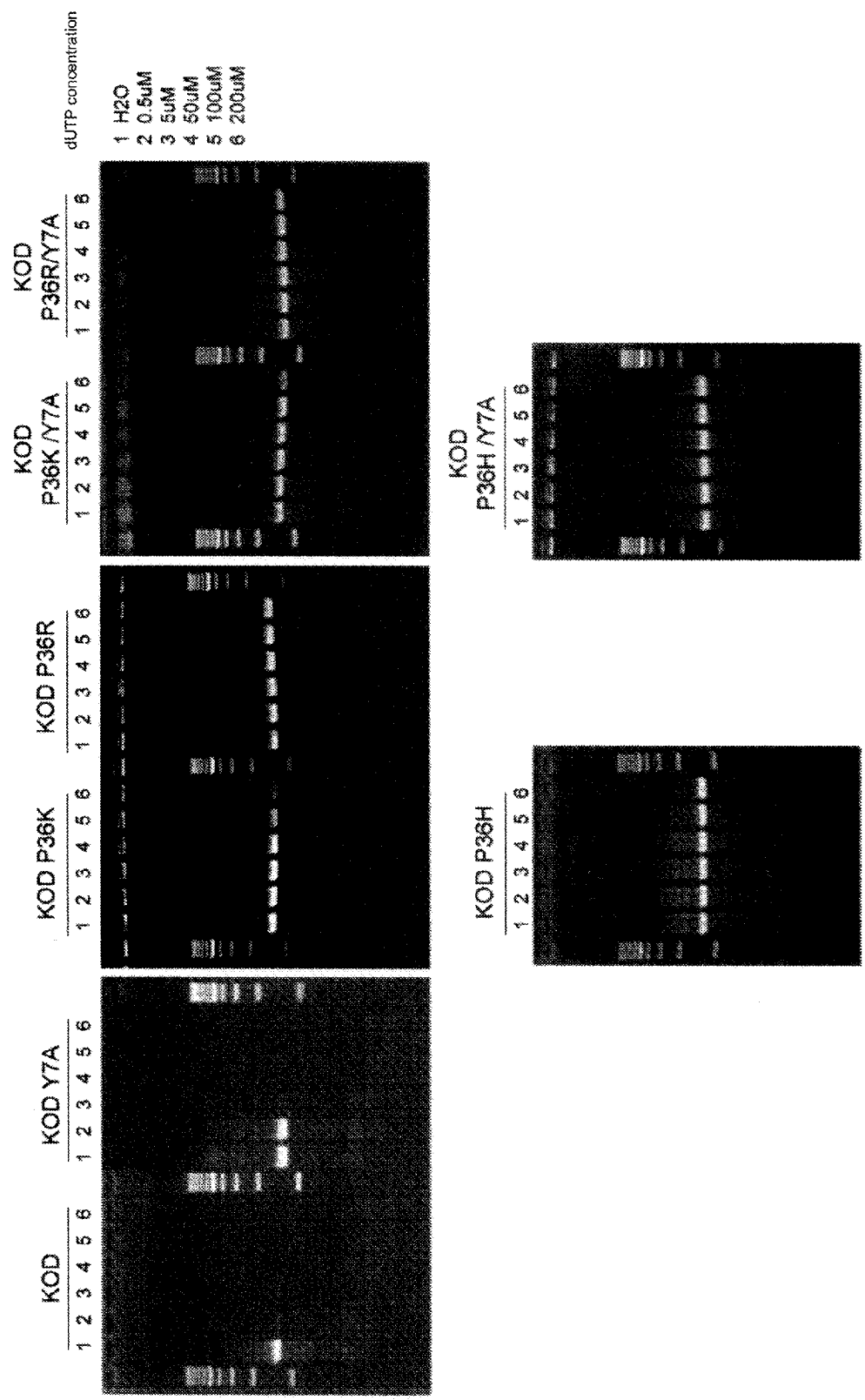
FIG. 3 illustrates amplification in PCR performed with the addition of dUTP to the reaction system to assess dUTP sensitivity.

The present invention relates to a modified DNA polymerase belonging to family B. DNA polymerases belonging to family B have polymerase regions and 3'-5' exonuclease (exo) regions in the enzyme molecule. Therefore, when incorrect bases are linked, DNA polymerases belonging to family B can remove the incorrect bases in the exo regions by proofreading. Accordingly, DNA polymerases belonging to family B are characterized by high-fidelity replication.

The DNA polymerase belonging to family B of the present invention is preferably a DNA polymerase derived from Archaea. DNA polymerases derived from Archaea belong to either family B Pol I type or Pol II type. In the present invention, the DNA polymerase preferably belongs to Pol I type. Examples of Archaea-derived DNA polymerases that belong to family B Pol I type include DNA polymerases isolated from bacteria of the genus *Pyrococcus* and the genus *Thermococcus*. Examples of DNA polymerases derived from the genus *Pyrococcus* include, but are not limited to, DNA polymerases isolated from *Pyrococcus furiosus, Pyrococcus* sp. GB-D, *Pyrococcus woesei, Pyrococcus abyssi,* and *Pyrococcus horikoshii*. Examples of DNA polymerases derived from the genus *Thermococcus* include, but are not limited to, DNA polymerases isolated from *Thermococcus kodakaraensis, Thermococcus gorgonarius, Thermococcus litoralis, Thermococcus* sp. JDF-3, *Thermococcus* sp. 9 degrees North-7 (*Thermococcus* sp. 9° N-7), *Thermococcus* sp. KS-1, *Thermococcus celer,* and *Thermococcus siculi*. PCR enzyme reagents containing such DNA polymerases are commercially available. Examples thereof include Pfu (Stratagene), KOD (Toyobo), Pfx (Life Technologies), Vent (New England Biolabs), Deep Vent (New England Biolabs), Tgo (Roche), Pwo (Roche), and the like.

The modified DNA polymerase of the present invention comprises amino acid sequences involved in uracil binding (uracil binding pockets). The amino acid sequences involved in uracil binding refer to amino acid sequences involved in recognition of dUTP. DNA polymerases derived from Archaea have a feature such that they stop an extension reaction when dUTP is present.

Uracil may be generated by thermal decomposition of cytosine. Since uracil pairs with adenine, change of cytosine to uracil by thermal decomposition causes mutation. It is assumed that since Archaea are thermophiles, such function is imparted to the DNA polymerases as a protective mechanism for growth at high temperatures. Uracil may also be generated from cytosine by thermal decomposition in thermal cycling of PCR. Under the influence of uracil generated by thermal decomposition, it has been impossible for Archaea-derived DNA polymerases that belong to family B to fully exhibit their high amplification efficiency in PCR.

The amino acid sequences involved in uracil binding are highly conserved in DNA polymerases derived from the genus *Pyrococcus* and DNA polymerases derived from the genus *Thermococcus*. In DNA polymerase derived from *Thermococcus kodakaraensis*, the amino acid sequences involved in uracil binding are formed by amino acids at positions 1 to 40 and amino acids at positions 78 to 130 in the amino acid sequence represented by SEQ ID NO: 1. In DNA polymerase derived from *Pyrococcus furiosus*, the amino acid sequences involved in uracil binding are formed by amino acids at positions 1 to 40 and amino acids at positions 78 to 130 in the amino acid sequence represented by SEQ ID NO: 2. In DNA polymerase derived from *Thermococcus gorgonarius*, the amino acid sequences involved in uracil binding are formed by amino acids at positions 1 to 40 and amino acids at positions 78 to 130 in the amino acid sequence represented by SEQ ID NO: 3. In DNA polymerase derived from *Thermococcus litoralis*, the amino acid sequences involved in uracil binding are formed by amino acids at positions 1 to 40 and amino acids at positions 78 to 130 in the amino acid sequence represented by SEQ ID NO: 4. In DNA polymerase derived from *Pyrococcus* sp. GB-D, the amino acid sequences involved in uracil binding are formed by amino acids at positions 1 to 40 and amino acids at positions 78 to 130 in the amino acid sequence represented by SEQ ID NO: 5. In DNA polymerase derived from *Thermococcus* sp. JDF-3, the amino acid sequences involved in uracil binding are formed by amino acids at positions 1 to 40 and amino acids at positions 78 to 130 in the amino acid sequence represented by SEQ ID NO: 6. In DNA polymerase derived from *Thermococcus* sp. 9° N-7, the amino acid sequences involved in uracil binding are formed by amino acids at positions 1 to 40 and amino acids at positions 78 to 130 in the amino acid sequence represented by SEQ ID NO: 7. In DNA polymerase derived from *Thermococcus* sp. KS-1, the amino acid sequences involved in uracil binding are formed by amino acids at positions 1 to 40 and amino acids at positions 78 to 130 in the amino acid sequence represented by SEQ ID NO: 8. In DNA polymerase derived from *Thermococcus celer*, the amino acid sequences involved in uracil binding are formed by amino acids at positions 1 to 40 and amino acids at positions 78 to 130 in the amino acid sequence represented by SEQ ID NO: 9. In DNA polymerase derived from *Thermococcus siculi*, the amino acid sequences involved in uracil binding are formed by amino acids at positions 1 to 40 and amino acids at positions 78 to 130 in the amino acid sequence represented by SEQ ID NO: 10. FIG. 1 shows a comparison of these amino acid sequences involved in uracil binding in SEQ ID NOs: 1 to 10. The present invention also encompasses DNA polymerases other than the DNA polymerases specifically shown in FIG. 1.

In these sequences, it is considered from data such as crystal structure analysis that amino acids corresponding to positions 7, 36, 37, 90 to 97, and 112 to 119 in the amino acid sequence represented by SEQ ID NO: 1 are directly associated with interaction with uracil. The expression "amino acids corresponding to positions 7, 36, 37, 90 to 97, and 112 to 119 in the amino acid sequence represented by SEQ ID NO: 1" encompasses, in a DNA polymerase having an amino acid sequence that is not completely identical to the amino acid sequence represented by SEQ ID NO: 1, amino acids corresponding to positions 7, 36, 37, 90 to 97, and 112 to 119 in SEQ ID NO: 1, the amino acids being involved in uracil binding.

The modified DNA polymerase of the present invention preferably comprises an amino acid sequence wherein at least one amino acid is modified in amino acid sequences involved in uracil binding that are amino acids corresponding to positions 1 to 40 and positions 78 to 130 in the amino acid sequence represented by SEQ ID NO: 1. More preferably, the modified DNA polymerase of the present invention comprises an amino acid sequence wherein at least one amino acid is modified among amino acids corresponding to positions 7, 36, 37, 90 to 97, and 112 to 119 in the amino acid sequence represented by SEQ ID NO: 1. The expression "amino acid is modified" encompasses amino acid substitution, deletion, and addition.

The modified DNA polymerase of the present invention more preferably comprises an amino acid sequence wherein at least two amino acids selected from the group consisting of amino acids corresponding to Y7, P36, and V93 in SEQ ID NO: 1 are modified. Here, for example, Y7 means the amino acid at position 7, tyrosine (Y) residue. The single alphabetical letters indicate commonly used amino acid abbreviations. As for Y7 amino acid, tyrosine (Y) is preferably substituted with a nonpolar amino acid, more specifically, a Y7A, Y7G, Y7V, Y7L, Y7I, Y7P, Y7F, Y7M, Y7W, or Y7C amino acid substitution. Here for example, Y7A means that the amino acid at position 7, tyrosine (Y) is substituted with alanine (A). The same applies hereafter. As for P36 amino acid, proline (P) is preferably substituted with a polar amino acid with positive charge, more specifically, a P36H, P36K, or P36R amino acid substitution. As for V93 amino acid, valine (V) is preferably substituted with a polar amino acid with positive charge, more specifically, a V93H, V93K, V93Q, or V93R amino acid substitution.

The expression "amino acids corresponding to Y7, P36, and V93 in SEQ ID NO: 1" encompasses, in a DNA polymerase comprising an amino acid sequence that is not completely identical to the amino acid sequence represented by SEQ ID NO: 1, amino acids corresponding to Y7, P36, and V93 in SEQ ID NO: 1, the amino acids being involved in uracil binding. The term "corresponding" refers to being at the same position when comparing the amino acid sequence with that of SEQ ID NO: 1.

The modified DNA polymerase of the present invention more preferably comprises an amino acid sequence comprising at least two modifications selected from the group consisting of amino acid modifications corresponding to Y7A, P36H, P36K, P36R, V93Q, V93K and V93R in SEQ ID NO: 1. Particularly preferably, the modified DNA polymerase of the present invention comprises an amino acid sequence comprising amino acid modifications corresponding to P36H/Y7A, P36K/Y7A, P36R/Y7A, V93Q/Y7A, V93K/Y7A, V93R/Y7A, or P36H/V93K in SEQ ID NO: 1.

In other words, the modified DNA polymerase of the present invention more preferably comprises at least two amino acid substitutions selected from (a) to (c) below:
(a) Y7A,
(b) P36H, P36R, or P36K, and
(c) V93K, V93Q, V93R, or V93H.

In another embodiment, the modified DNA polymerase of the present invention more preferably comprises an amino acid sequence wherein an amino acid corresponding to P36 in SEQ ID NO: 1 is modified. Particularly preferably, the modified DNA polymerase of the present invention comprises an amino acid sequence comprising an amino acid modification corresponding to P36H, P36R, or P36K in SEQ ID NO: 1. In other words, the modified DNA polymerase of the present invention particularly preferably comprises a P36H, P36R, or P36K amino acid substitution.

The modified DNA polymerase with modification in the amino acid sequences involved in uracil binding is characterized by low uracil sensitivity compared to wild-type DNA polymerase. Low uracil sensitivity means that no substantial deterioration in the function of an Archaea-derived DNA polymerase belonging to family B is observed even in the presence of dUTP, and that the effect of dUTP on an extension reaction of the DNA polymerase is reduced.

The uracil sensitivity of the modified DNA polymerase of the present invention can be evaluated by PCR. For example, a dUTP solution is added at a final concentration of 0.5 µM to 200 µM to a common PCR reaction solution containing DNA as a template, a buffer, magnesium, dNTPs, primers, and a DNA polymerase to be evaluated, and thermal cycling is performed. After the reaction, the presence or absence of PCR products is confirmed by ethidium bromide-stained agarose electrophoresis, and the uracil sensitivity can be evaluated by the concentration of accepted dUTP. With a DNA polymerase having high uracil sensitivity, the extension reaction is inhibited by the addition of a small amount of dUTP, and PCR products cannot be confirmed. With a DNA polymerase having low uracil sensitivity, gene amplification by PCR can be confirmed without problem, even if a high concentration of dUTP is added. The modified DNA polymerase with low uracil sensitivity in the present invention refers to a DNA polymerase such that when optimum thermal cycling is performed using any primers and DNA as a template in a reaction buffer optimum for the enzyme, even if a high concentration of dUTP is added, an extension reaction is not inhibited and PCR products can be confirmed, compared to wild-type DNA polymerase, which has no mutation.

More specifically, 10×PCR buffer included in KOD-Plus-Ver.-2 (produced by Toyobo Co. Ltd.) or 10×PCR buffer included in Pfu DNA Polymerase (produced by Agilent) is used; dUTP (produced by Roche) is added to 50 µl of individual reaction solutions containing 1×PCR buffer, 1.5 mM MgSO$_4$, dNTPs (dATP, dTTP, dCTP, and dGTP) in an amount of 0.2 mM, primers represented by SEQ ID NOs: 25 and 26 in an amount of 15 pmol for amplifying about 1.3 kb, 10 ng of human genomic DNA (produced by Roche), and 1 U of each respective enzyme, to final concentrations of 0.5, 5, 50, 100, and 200 µM. PCR is performed using a GeneAmp PCR system 9700 (Applied Biosystems) on the following schedule: preliminary reaction at 94° C. for 30 seconds, followed by 30 cycles, each cycle consisting of 98° C. for 10 seconds, 65° C. for 30 seconds, and 68° C. for 1 minute and 30 seconds. After the completion of each individual reaction, 5 µl of each of the resulting reaction solutions is subjected to agarose electrophoresis, followed by ethidium bromide staining. The uracil sensitivity can be evaluated by confirming amplified DNA fragments of about 1.3 kb under ultraviolet irradiation.

The modified DNA polymerase of the present invention comprises amino acid sequences involved in 3'-5' exonuclease activity (3'-5' exonuclease regions). "3'-5' exonuclease activity" refers to the ability to remove incorporated nucleotides from the 3' end of a DNA polymer. The 3'-5' exonuclease regions are highly conserved in DNA polymerases belonging to family B. The 3'-5' exonuclease regions are formed by amino acids at positions 137 to 147, 206 to 222, and 308 to 318 in DNA polymerase derived from *Thermococcus kodakaraensis* (SEQ ID NO: 1), DNA polymerase derived from *Pyrococcus furiosus* (SEQ ID NO: 2), DNA polymerase derived from *Thermococcus gorgonarius* (SEQ ID NO: 3), DNA polymerase derived from *Thermococcus litoralis* (SEQ ID NO: 4), DNA polymerase derived from *Pyrococcus* sp. GB-D (SEQ ID NO: 5), DNA polymerase derived from *Thermococcus* sp. JDF-3 (SEQ ID NO: 6), DNA polymerase derived from *Thermococcus* sp. 9° N-7 (SEQ ID NO: 7), DNA polymerase derived from *Thermococcus* sp. KS-1 (SEQ ID NO: 8), DNA polymerase derived from *Thermococcus celer* (SEQ ID NO: 9), and DNA polymerase derived from *Thermococcus siculi* (SEQ ID NO: 10). FIG. 2 shows a comparison of amino acid sequences for the 3'-5' exonuclease regions in SEQ ID NOs: 1 to 10. The present invention also encompasses DNA polymerases other than the DNA polymerases having sequences specifically shown in FIG. 2. In Archaea-derived DNA polymerases that belong to family B other than the DNA polymerases having the amino acid sequences represented by SEQ ID NOs: 1 to 10, the 3'-5' exonuclease regions refer to those corresponding to 3'-5' exonuclease regions that are amino acids corresponding to positions 137 to 147, 206 to 222, and 308 to 318 represented by SEQ ID NO: 1.

The expression "amino acids corresponding to positions 137 to 147, 206 to 222, and 308 to 318 represented by SEQ ID NO: 1" encompasses, in a DNA polymerase comprising an amino acid sequence that is not completely identical to the amino acid sequence represented by SEQ ID NO: 1, amino acids corresponding to positions 137 to 147, 206 to 222, and 308 to 318 in SEQ ID NO: 1.

The modified DNA polymerase of the present invention preferably comprises an amino acid sequence wherein one or more of the 3'-5' exonuclease regions are modified in addition to the above-mentioned at least one modification in the amino acid sequences involved in uracil binding. The expression "one or more of 3'-5' exonuclease regions are modified" encompasses at least one amino acid substitution, deletion, and addition in the amino acid sequences involved in 3'-5' exonuclease activity.

The modified DNA polymerase of the present invention more preferably comprises an amino acid sequence wherein at least one amino acid among amino acids corresponding to positions 137 to 147, 206 to 222, and 308 to 318 in SEQ ID NO: 1 is modified, in addition to the above-mentioned at least one modification in the amino acid sequences involved in uracil binding. More preferably, the modified DNA polymerase of the present invention comprises an amino acid sequence wherein at least one amino acid among amino acids corresponding to D141, I142, E143, H147, N210, and Y311 in SEQ ID NO: 1 is modified. Particularly preferably, the modified DNA polymerase of the present invention comprises an amino acid sequence comprising amino acid modification(s) corresponding to D141A/E143A, I142R, N210D, or Y311F in SEQ ID NO: 1. These modified DNA polymerases are DNA polymerases that are deficient in 3'-5' exonuclease activity. In addition, the modified DNA polymerase of the present invention may comprise an amino acid sequence comprising an amino acid modification corresponding to H147E or H147D; such a modified DNA polymerase maintains 3'-5' exonuclease activity and is a DNA polymerase with improved PCR efficiency.

The expression "amino acids corresponding to D141, I142, E143, H147, N210, and Y311 in SEQ ID NO: 1" encompasses, in a DNA polymerase having an amino acid sequence that is not completely identical to the amino acid sequence represented by SEQ ID NO: 1, amino acids corresponding to D141, I142, E143, H147, N210, and Y311 in SEQ ID NO: 1.

In the words, the modified DNA polymerase of the present invention more preferably comprises, in addition to the at least one modification in the amino acid sequences involved in uracil binding, at least one amino acid substitution selected from (d) so (g) below:
(d) D141A and E143A,
(e) I142R,
(f) N210D, and
(g) H147E or H147D.

A DNA polymerase that is deficient in 3'-5' exonuclease activity (exo(−)) may completely lack 3'-5' exonuclease activity or have 0.03%, 0.05%, 0.1%, 1%, 5%, 10%, 20% or up to at most 50% of 3'-5' exonuclease activity compared to the parental enzyme. A method for producing and analyzing a DNA polymerase that is deficient in 3'-5' exonuclease activity is disclosed in Patent Literature 3 or the like. A DNA polymerase with improved PCR efficiency refers to a modified DNA polymerase with which the amount of PCR products is increased compared to the parental enzyme. JP3891330B discloses a method for analysis therefor.

As a method for producing such modified enzymes, hitherto-known methods are usable. For example, there is a method for producing a mutated (modified) DNA polymerase with a new function by a protein engineering technique by introducing a mutation into a gene encoding a wild-type DNA polymerase.

As an embodiment of the method for introducing amino acid modifications, inverse PCR-based site-directed mutagenesis can be used. For example, KOD-Plus-Mutagenesis Kit (produced by Toyobo Co. Ltd.) is a kit to obtain a transformant carrying a plasmid into which the desired mutation is introduced, by the following: (1) denaturing a plasmid into which a target gene is inserted, annealing mutant primers to the plasmid, and subsequently performing an extension reaction with a KOD DNA polymerase; (2) repeating the cycle of (1) 15 times; (3) selectively cleaving only the plasmid as a template with restriction enzyme DpnI; (4) circularizing the newly synthesized gene by phosphorylation and ligation; and (5) transforming the circularized gene into *Escherichia coli*.

The modified DNA polymerase gene is, if necessary, transferred to an expression vector; afterward, *Escherichia coli*, for example, as a host is transformed with the expression vector, and then applied to an agar medium containing a drug such as ampicillin to form colonies. The colonies are inoculated into a nutrient medium, for example, an LB medium or a 2× YT medium, and cultured at 37° C. for 12 to 20 hours. Thereafter, the bacterial cells are disrupted to extract a crude enzyme solution. As the vector, those derived from pBluescript are preferable. As a method for disrupting the cells, any known technique may be used. For example, sonication, French press disruption, glass bead disruption, and like physical disruption methods, and lytic enzymes such as lysozyme are usable. This crude enzyme solution is heat treated at 80° C. for 30 minutes to deactivate the polymerase derived from the host, and DNA polymerase activity is measured.

As a method for obtaining a purified DNA polymerase from the strain selected by the above-mentioned method, any technique may be used. Examples thereof include the following method. The bacterial cells obtained after culturing on the nutrient medium are collected and disrupted by an enzymatic or physical disruption method to extract a crude enzyme solution. A DNA polymerase fraction is collected from the obtained crude enzyme extract by performing heat treatment, for example, at 80° C. for 30 minutes, followed by ammonium sulfate precipitation. This crude enzyme solution can be desalted by a method such as gel filtration with Sephadex G-25 (produced by Amersham Pharmacia Biotech). After this operation, separation and purification are performed by heparin-Sepharose column chromatography to obtain a purified enzyme sample. The purified enzyme sample is purified to such an extent that the sample nearly shows a single band in SDS-PAGE.

The present invention can be used not only in PCR, but also in a method in which a DNA primer extension product is synthesized by performing a reaction using DNA as template, one primer, and deoxyribonucleotide triphosphates (dNTPs) to extend the primer. Specific examples include primer extension, sequencing, methods in which conventional temperature cycling is not performed, and cycle sequencing.

The modified DNA polymerase of the present invention may be provided in the form of a reagent for amplifying nucleic acids. Examples of the reagent for amplifying nucleic acids include a reagent containing two primers, one of which is complementary to all or a portion of a DNA extension product of the other primer, dNTPs, the modified DNA polymerase of the present invention as described above, a divalent ion, a monovalent ion, and a buffer. Specific examples include a reagent containing two primers, one of which is complementary to a DNA extension product of the other primer, dNTPs, the above-mentioned modified DNA polymerase, magnesium ion, ammonium ion and/or potassium ion, BSA, a nonionic surfactant as described above, and a buffer.

In another embodiment of the reagent for amplifying nucleic acids, the reagent for amplifying nucleic acids contains two primers, one of which is complementary to all or a portion of a DNA extension product of the other primer, dNTPs, the modified DNA polymerase of the present invention as described above, divalent ion, a monovalent ion, a buffer, and, if necessary, an antibody with activity that suppresses polymerase activity and/or 3'-5' exonuclease activity of the modified DNA polymerase. Examples of antibodies include monoclonal antibodies, polyclonal antibodies, and the like. The present reagent for amplifying nucleic acids is effective, in particular, in increasing PCR sensitivity and reducing nonspecific amplification.

In addition, the reagent for amplifying nucleic acids of the present invention may be provided in the form of a kit. Examples of the kit include those comprising the above-mentioned reagent for amplifying nucleic acids, and further, if necessary, dUTP and uracil-DNA glycosylase to be used for dUTP/UNG decontamination methods. Examples of the kit also include those comprising the above-mentioned reagent for amplifying nucleic acids, and further comprising internal control nucleic acid (template) as an internal control and a primer pair for amplifying the internal control nucleic acid.

The modified DNA polymerase of the present invention can find application in, for example, the following fields.
PCR Using Inosine (dITP)-Containing Primers PCR with degenerate primers is used as a technique for cloning, from a known amino acid sequence, the gene thereof. In PCR with degenerate primers, inosine (dITP)-containing primers are often used to reduce the number of degenerate primer combinations. Since inosine does not form a complementary pair with any base and does not inhibit double strand formation, a plurality of types of codons for amino acids can be comprehensively amplified. However, wild-type DNA, polymerases derived from the genus *Pyrococcus* or the genus *Thermococcus* have a problem such that the reactivity is significantly reduced when inosine-containing primers are used. The modified DNA polymerase of the present invention, however, exhibits high amplification efficiency as well as high fidelity, even if inosine-containing primers are used. Accordingly, the present invention is useful for PCR using inosine-containing primers.

Amplification Reaction of Bisulfite-Treated DNA

Techniques for DNA methylation analysis include bisulfite sequencing (BSP), in which genomic DNA is subjected to bisulfite treatment to analyze the presence or absence and position of methylation, and methylation-specific PCR (MSP), in which methylated and unmethylated bases are specifically PCR-amplified to analyze methylation status. When genomic DNA is subjected to bisulfite treatment, unmethylated cytosine is converted to uracil, whereas methylated cytosine is not converted. Thus, methylation analysis can be performed based on the difference of cytosine and thymine (uracil) before and after bisulfite treatment. Since the modified DNA polymerase of the present invention can effectively amplify DNA containing uracil, it is useful for amplification reactions of bisulfite-treated DNA and methylation analysis techniques.

Use for dUTP/UNG Decontamination Methods

To prevent PCR carryover, dUTP/UNG decontamination methods are used in PCR. dUTP/UNG decontamination methods prevent carryover by performing a PCR reaction while incorporating uracil (dUTP), and degrading contaminant PCR products with uracil-DNA glycosylase (UNG) before the next PCR reaction is performed. UNG degrades uracil-glycosidic bonds in single- or double-stranded DNA, excising uracil and creating alkali-sensitive abasic sites in the DNA. Since the modified DNA polymerase of the present invention can effectively amplify DNA containing uracil, it is useful for dUTP/UNG decontamination methods.

[Method for Measuring DNA Polymerase Activity]

DNA polymerase activity is measured by the following steps (1) to (4). If the enzyme activity in a sample is high, activity measurement is carried out after the sample is diluted with a storage buffer (50 mM Tris-HCl (pH 8.0), 50 mM KCl, 1 mM dithiothreitol, 0.1% Tween 20, 0.1% Nonidet P40, 50% glycerin).

(1) To a microtube, 25 µl of Solution A shown below, 5 µl of Solution B shown below, 5 µl of Solution C shown below, 10 µl of sterile water, and 5 µl of an enzyme solution are added, and reacted at 75° C. for 10 minutes.
(2) Thereafter, the resulting mixture is ice-cooled, 50 µl of Solution E and 100 µl of Solution D are added thereto, and the mixture is stirred, followed by further ice-cooling for 10 minutes.
(3) The solution is filtered through a glass filter (GF/C filter, produced by Whatman), and the filter is washed sufficiently with 0.1 N hydrochloric acid and ethanol.
(4) The radioactivity of the filter is measured with a liquid scintillation counter (produced by Packard) to determine the incorporation of nucleotides into the template DNA. 1 unit of enzyme activity is defined as the amount of enzyme that catalyzes the incorporation of 10 nmol of nucleotides into an acid-insoluble fraction (i.e., a fraction which becomes insoluble when Solution D is added) per 30 minutes under the above conditions.

A: 40 mM Tris-HCl buffer (pH 7.5), 16 mM magnesium chloride, 15 mM dithiothreitol, 100 µg/ml BSA (bovine serum albumin)
B: 1.5 µg/µl activated calf thymus DNA
C: 1.5 mM dNTP (250 cpm/pmol [3H]dTTP)
D: 20% trichloroacetic acid (2 mM sodium pyrophosphate)
E: 1 mg/ml calf thymus DNA

EXAMPLES

The present invention will be described below in detail with reference to Examples.

Production Example 1

Preparation of KOD Y7A Mutant

A plasmid containing a modified DNA polymerase gene derived from *Thermococcus kodakaraensis* KOD1 strain, pKOD Y7A (plasmid containing a modified DNA polymerase gene in which TAC at positions 19 to 21 in SEQ ID NO: 11 was substituted with GCC) was prepared.

A modified DNA polymerase gene derived from *Thermococcus kodakaraensis* KOD1 strain cloned into pBluescript (SEQ ID NO: 11) (pKOD) was used as a DNA template used for mutagenesis. Mutagenesis was conducted with a KOD-Plus-Mutagenesis kit (produced by Toyobo Co. Ltd.) in accordance with the instruction manual. Mutagenesis primers used were primers represented by SEQ ID NOs: 13 and 14. The mutant was confirmed by determining its nucleotide sequence. *Escherichia coli* JM109 was transformed with the obtained plasmid, and used for enzyme preparation.

Production Example 2

Preparation of Modified DNA Polymerase (KOD Y7A)

The bacterial cells obtained in Production Example 1 were cultured by the following process.

First, *Escherichia coli* JM109 (strain transformed with the plasmid) obtained in Production Example 1 was cultured in 3 ml of an LB medium containing 100 µg/ml of ampicillin (1% Bacto-tryptone, 0.5% yeast extract, 0.5% sodium chloride; produced by Gibco) at 37° C. for 16 hours. Next, 80 mL of a sterilized TB medium containing 100 µg/ml of ampicillin (Molecular Cloning, second edition, p. A2) was introduced into a 500-mL Sakaguchi flask. Thereafter, the cultured *Escherichia coli* JM109 (strain transformed with the plasmid) was inoculated into the TB medium (using a test tube), and an aeration culture was conducted at 37° C. for 15 hours.

From the bacterial cells cultured by the above procedure, a purified modified DNA polymerase was obtained in the following manner.

The bacterial cells were collected from the culture medium by centrifugation, suspended in 50 ml of a disruption buffer (30 mM Tris-HCl buffer (pH 8.0), 30 mM NaCl, 0.1 mM EDTA), and disrupted by sonication, thus obtaining a cell disruption solution. Subsequently, the cell disruption solution was treated at 80° C. for 15 minutes, after which the insoluble fraction was removed by centrifugation. Nucleic acid removal using polyethyleneimine, ammonium sulfate precipitation, and heparin-Sepharose chromatography were then carried out. Finally, replacement by a storage buffer (50 mM Tris-HCl buffer (pH 8.0), 50 mM potassium chloride, 1 mM dithiothreitol, 0.1% Tween 20, 0.1% Nonidet P40, 50% glycerin) was carried out. A modified DNA polymerase (KOD Y7A) was thereby obtained.

In the purification described above, the measurement of DNA polymerase activity was conducted in the manner as described below. When the enzyme activity was high, the sample was measured after dilution.

(Reagent)

Solution A: 40 mM Tris-HCl buffer (pH 7.5), 16 mM magnesium chloride, 15 mM dithiothreitol, 100 µg/ml BSA Solution B: 1.5 µg/µl activated calf thymus DNA Solution C: 1.5 mM dNTP (250 cpm/pmol [3H]dTTP)
Solution D: 20% trichloroacetic acid (2 mM sodium pyrophosphate)
Solution E: 1 mg/ml calf thymus DNA
(Method)

To a microtube, 25 µl of Solution A, 5 µl of Solution B, 5 µl of Solution C, and 10 µl of sterile water were added, and the mixture was stirred. Thereafter, 5 µl of the above-mentioned purified enzyme diluted solution was added thereto, and reacted at 75° C. for 10 minutes. The resulting mixture was then cooled, 50 µl of Solution E and 100 µl of Solution D were added thereto, and the mixture was stirred, followed by further ice-cooling for 10 minutes. The solution was filtered through a glass filter (GF/C filter produced by Whatman), and the filter was washed sufficiently with 0.1 N hydrochloric acid and ethanol. The radioactivity of the filter was measured with a liquid scintillation counter (produced by Packard) to determine the incorporation of nucleotides into the template DNA. 1 unit of enzyme activity was defined as the amount of enzyme that catalyzes the incorporation of 10 nmol of nucleotides into an acid-insoluble fraction per 30 minutes under the above conditions.

Production Example 3

Preparation of KOD P36H pKOD P36H (plasmid containing a modified DNA polymerase gene in which CCC at positions 106 to 108 in SEQ ID NO: 11 was substituted with CAC) was prepared in the same manner as in Production Example 2. pKOD was used as a template, and primers represented by SEQ ID NOs: 15 and 18 were used as mutagenesis primers. Further, a modified DNA polymerase (KOD P36H) was obtained using the same purification method as in Production Example 2.

Production Example 4

Preparation of KOD P36K pKOD P36K (plasmid containing a modified DNA polymerase gene in which CCC at positions 106 to 108 in SEQ ID NO: 11 was substituted with AAA) was prepared in the same manner as in Production Example 2. pKOD was used as a template, and primers represented by SEQ ID NOs: 16 and 18 were used as mutagenesis primers. Further, a modified DNA polymerase (KOD P36K) was obtained using the same purification method as in Production Example 2.

Production Example 5

Preparation of KOD P36R pKOD P36R (plasmid containing a modified DNA polymerase gene in which CCC at positions 106 to 108 in the SEQ ID NO: 11 was substituted with CGT) was prepared in the same manner as in Production Example 2. pKOD was used as a template, and primers represented by SEQ ID NOs: 17 and 18 were used as mutagenesis primers. Further, a modified DNA polymerase (KOD P36R) was obtained using the same purification method as in Production Example 2.

Production Example 6

Preparation of KOD V93Q pKOD V93Q (plasmid containing a modified DNA polymerase gene in which GTC at positions 277 to 279 in SEQ ID NO: 11 was substituted with CAG) was prepared in the same manner as in Production Example 2. pKOD was used as a template, and primers represented by SEQ ID NOs: 19 and 20 were used as mutagenesis primers. Further, a modified DNA polymerase (KOD V93Q) was obtained using the same purification method as in Production Example 2.

Production Example 7

Preparation of KOD V93K pKOD V93K (plasmid containing a modified DNA polymerase gene in which GTC at positions 277 to 279 in SEQ ID NO: 11 was substituted with AAA) was prepared in the same manner as in Production Example 2. pKOD was used as a template, and primers represented by SEQ ID NOs: 19 and 21 were used as mutagenesis primers. Further, a modified DNA polymerase (KOD V93K) was obtained using the same purification method as in Production Example 2.

Production Example 8

Preparation of KOD V93R pKOD V93R (plasmid containing a modified DNA polymerase gene in which GTC at positions 277 to 279 in SEQ ID NO: 11 was substituted with CGT) was prepared in the same manner as in Production Example 2. pKOD was used as a template, and primers represented by SEQ ID NOs: 19 and 22 were used as mutagenesis primers. Further, a modified DNA polymerase (KOD V93R) was obtained using the same purification method as in Production Example 2.

Production Example 9

Preparation of KOD P115Δ pKOD P115Δ (plasmid containing a modified DNA polymerase gene that lacked CCC at positions 343 to 345 in SEQ ID NO: 11) was prepared in the same manner as in Production Example 2. pKOD was used as a template, and primers represented by SEQ ID NOs: 23 and 25 were used as mutagenesis primers. Further, a modified DNA polymerase (KOD P115Δ) was obtained using the same purification method as in Production Example 2.

Production Example 10

Preparation of KOD Y7A/P36H pKOD Y7A/P36H (plasmid containing a modified DNA polymerase gene in which TAC at Positions 19 to 21 in SEQ ID NO: 11 was substituted with GCC, and CCC at positions 106 to 108 in SEQ ID NO: 11 was substituted with CAC) was prepared in the same manner as in Production Example 2. pKOD Y7A was used as a template, and primers represented by SEQ ID NOs: 15 and 18 were used as mutagenesis primers. Further, a modified DNA polymerase (KOD Y7A/P36H) was obtained using the same purification method as in Production Example 2.

Production Example 11

Preparation of KOD Y7A/P36K pKOD Y7A/P36K (plasmid containing a modified DNA polymerase gene in which TAC at positions 19 to 21 in SEQ ID NO: 11 was substituted with GCC, and CCC at positions 106 to 108 in SEQ ID NO: 11 was substituted with AAA) was prepared in the same manner as in Production Example 2. pKOD Y7A was used as a template, and primers represented by SEQ ID NOs: 16 and 18 were used as mutagenesis primers. Further, a modified DNA polymerase (KOD Y7A/P36K) was obtained using the same purification method as in Production Example 2.

Production Example 12

Preparation of KOD Y7A/P36R pKOD Y7A/P36R (plasmid containing a modified DNA polymerase gene in which TAC at positions 19 to 21 in SEQ ID NO: 11 was substituted with GCC, and CCC at positions 106 to 108 in SEQ ID NO: 11 was substituted with CGT) was prepared in the same manner as in Production Example 2 (pKOD Y7A/P36R). pKOD Y7A was used as a template, and primers represented by SEQ ID NOs: 17 and 18 were used as mutagenesis primers. Further, a modified DNA polymerase (KOD Y7A/P36R) was obtained using the same purification method as in Production Example 2.

Production Example 13

Preparation of KOD Y7A/V93K pKOD Y7A/V93K (plasmid containing a modified DNA polymerase gene in which TAC at positions 19 to 21 in SEQ ID NO: 11 was substituted with GCC, and GTC at positions 277 to 279 in SEQ ID NO: 11 was substituted with AAA) was prepared in the same manner as in Production Example 2. pKOD Y7A was used as a template, and primers represented by SEQ ID NOs: 19 and 21 were used as mutagenesis primers. Further, a modified DNA polymerase (KOD Y7A/V93K) was obtained using the same purification method as in Production Example 2.

Production Example 14

Preparation of KOD Y7A/P115Δ pKOD Y7A/P115Δ (plasmid containing a modified DNA polymerase gene in which TAC at positions 19 to 21 in SEQ ID NO: 11 was substituted with GCC, and that lacked CCC at positions 343 to 345 in SEQ ID NO: 11) was prepared in the same manner as in Production Example 2. pKOD Y7A was used as a template, and primers represented by SEQ ID NOs: 23 and 24 were used as mutagenesis primers. Further, a modified DNA polymerase (KOD Y7A/P115Δ) was obtained using the same purification method as in Production Example 2.

Production Example 15

Preparation of KOD P36H/V93K pKOD P36H/V3K (plasmid containing a modified DNA polymerase gene in which CCC at positions 106 to 108 in SEQ ID NO: 11 was substituted with CAC, and GTC at positions 277 to 279 in SEQ ID NO: 11 was substituted with AAA) was prepared in the same manner as in Production Example 2. pKOD V93K was used as a template, and primers represented by SEQ ID NOs: 15 and 18 were used as mutagenesis primers. Further, a modified DNA polymerase (KOD P36H/V93K) was obtained using the same purification method as in Production Example 2.

Production Example 16

Preparation of KOD P36R/V93K pKOD P36R/V93K (plasmid containing a modified DNA polymerase gene in which CCC at positions 106 to 108 in SEQ ID NO: 11 was substituted with CGT, and GTC at positions 277 to 279 in SEQ ID NO: 11 was substituted with AAA) was prepared in the same manner as in Production Example 2. pKOD V93K was used as a template, and primers represented by SEQ ID NOs: 17 and 18 were used as mutagenesis primers. Further, a modified DNA polymerase (KOD P36R/V93K) was obtained using the same purification method as in Production Example 2.

Production Example 17

Preparation of KOD Y7A/P36H/V93K pKOD Y7A/P36H/V93K (plasmid containing a modified DNA polymerase gene in which TAC at positions 19 to 21 in SEQ ID NO: 11 was substituted with GCC, CCC at positions 106 to 108 in SEQ ID NO: 11 was substituted with CAC, and GTC at positions 277 to 279 in SEQ ID NO: 11 was substituted with AAA) was prepared in the same manner as in Production Example 2. pKOD Y7A/V93K was used as a template, and primers represented by SEQ ID NOs: 15 and 18 were used as mutagenesis primers. Further, a modified DNA polymerase (KOD Y7A/P36H/V93K) was obtained using the same purification method as in Production Example 2.

Production Example 18

Preparation of KOD Y7A/P36R/V93K pKOD Y7A/P36R/V93K (plasmid containing a modified DNA polymerase gene in which TAC at positions 19 to 21 in SEQ ID NO: 11 was substituted with GCC, CCC at positions 106 to 108 in SEQ ID NO: 11 was substituted with CGT, and GTC at positions 277 to 279 in SEQ ID NO: 11 was substituted with AAA) was prepared in the same manner as in Production Example 2. pKOD Y7A/V93K was used as a template, and primers represented by SEQ ID NOs: 17 and 18 were used as mutagenesis primers. Further, a modified DNA polymerase (KOD Y7A/P36R/V93K) was obtained using the same purification method as in Production Example 2.

Production Example 19

Preparation of KOD N210D Mutants

KOD N210D is a modified DNA polymerase that comprises a modification in the 3'-5' exonuclease regions of the wild type KOD DNA polymerase and is deficient in 3'-5' exonuclease activity (exo(−)). Various mutations were inserted into pKOD N210D in the same manner as in Production Examples 1 to 18. pKOD N210D is a plasmid containing a modified DNA polymerase gene in which AAC at positions 628 to 630 in SEQ ID NO: 11 is substituted with GAC, and the sequence is disclosed in JP3487394B. Further, modified DNA polymerases were individually purified using the same purification method as in Production Example 2.

Production Example 20

Preparation of KOD D141A/E143A Mutants

KOD D141A/E143A is an (exo(−)) modified DNA polymerase that comprises modifications in the 3'-5' exonuclease regions of the wild-type KOD DNA polymerase and is deficient in 3'-5' exonuclease activity. Various mutations were inserted into pKOD D141A/E143A in the same manner as in Production Examples 1 to 18. pKOD D141A/E143A is a plasmid containing a modified DNA polymerase gene in which GAC at positions 421 to 423 in SEQ ID NO: 11 is substituted with GCC, and GAA at positions 427 to 429 in SEQ ID NO: 11 is substituted with GCA. Further, modified DNA polymerases were individually purified using the same purification method as in Production Example 2.

Production Example 21

Preparation of KOD I142R Mutants

KOD I142R is an (exo(−)) modified DNA polymerase that comprises a modification in the 3'-5' exonuclease regions of the wild-type KOD DNA polymerase and is deficient in 3'-5' exonuclease activity. Various mutations were inserted into pKOD I142R in the same manner as in Production Examples 1 to 18. pKOD I142R is a plasmid containing a modified DNA polymerase gene in which ATT at positions 424 to 426 in SEQ ID NO: 11 is substituted with CGT, and the sequence is disclosed in JP3487394B. Further, modified DNA polymerases were individually purified using the same purification method as in Production Example 2.

Production Example 21

Preparation of KOD H147E Mutants

KOD H147E is a modified DNA polymerase that comprises a modification in the 3'-5' exonuclease regions of the wild-type KOD DNA polymerase, but maintains 3'-5' exonuclease activity. Various mutations were inserted into pKOD H147E in the same manner as in Production Examples 1 to 18. pKOD H147E is a plasmid containing a modified DNA polymerase gene in which CAT at positions 439 to 442 in SEQ ID NO: 11 is substituted with GAG, and the sequence is disclosed in JP3891330B. Further, modified DNA polymerases were individually purified using the same purification method as in Production Example 2.

Production Example 22

Preparation of Pfu Y7A pPfu Y7A (plasmid containing a modified DNA polymerase gene in which TAC at positions 19 to 21 in SEQ ID NO: 12 was substituted with GCC) was prepared in the same manner as in Production Example 2 (pPfu Y7A). pPfu, a pBluescript plasmid into which the thermostable DNA polymerase gene represented by SEQ ID NO: 12 was cloned was used as a template, and primers represented by SEQ ID NOs: 32 and 33 were used as mutagenesis primers. Further, a modified DNA polymerase (Pfu Y7A) was obtained using the same purification method as in Production Example 2.

Production Example 23

Preparation of Pfu P36H pPfu P36H (plasmid containing a modified DNA polymerase gene in which CCA at positions 106 to 108 in SEQ ID NO: 12 was substituted with CAC) was prepared in the same manner as in Production Example 2. pPfu was used as a template, and primers represented by SEQ ID NOs: 34 and 35 were used as mutagenesis primers. Further, a modified DNA polymerase (Pfu P36H) was obtained using the same purification method as in Production Example 2.

Production Example 24

Preparation of Pfu V93R pPfu V93R (plasmid containing a modified DNA polymerase gene in which GTT at positions 277 to 279 in SEQ ID NO: 12 was substituted with CGT) was prepared in the same manner as in Production Example 2. pPfu was used as a template, and primers represented by SEQ ID NOs: 36 and 37 were used as mutagenesis primers. Further, a modified DNA polymerase (Pfu V93R) was obtained using the same purification method as in Production Example 2.

Production Example 25

Preparation of Pfu Y7A/P36H pPfu Y7A/P36H (plasmid containing a modified DNA polymerase gene in which TAC at positions 19 to 21 in SEQ ID NO: 12 was substituted with GCC, and CCA at positions 106 to 108 in SEQ ID NO: 12 was substituted with CAC) was prepared in the same manner as in Production Example 2. pPfu Y7A was used as a template, and primers represented by SEQ ID NOs: 34 and 35 were used as mutagenesis primers. Further, a modified DNA polymerase (Pfu Y7A/P36H) was obtained using the same purification method as in Production Example 2.

Production Example 26

Preparation of Pfu Y7A/V93K pPfu Y7A/V93K (plasmid containing a modified DNA polymerase gene in which TAC at positions 19 to 21 in SEQ ID NO: 12 was substituted with GCC, and GTT at positions 277 to 279 in SEQ ID NO: 12 was substituted with AAA) was prepared in the same manner as in Production Example 2. pPfu Y7A was used as a template, and primers represented by SEQ ID NOs: 36 and 37 were used as mutagenesis primers. Further, a modified DNA polymerase (Pfu Y7A/V93K) was obtained using the same purification method as in Production Example 2.

Production Example 27

Preparation of Pfu N210D/Y7A/P36H pPfu N210D/Y7A/P36H (plasmid containing a modified DNA polymerase gene in which TAC at positions 19 to 21 in SEQ ID NO: 12 was substituted with GCC, CCA at positions 106 to 108 in SEQ ID NO: 12 was substituted with CAC, and AAT at positions 628 to 630 in SEQ ID NO: 12 was substituted with GAC) was prepared in the same manner as in Production Example 2. pPfu Y7A/P36H was used as a template, and primers represented by SEQ ID NOs: 38 and 39 were used as mutagenesis primers. Further, a modified DNA polymerase (Pfu N210D/Y7A/P36H) was obtained using the same purification method as in Production Example 2.

Production Example 28

Preparation of Pfu N210D/Y7A/V93K pPfu N210D/Y7A/V93K (plasmid containing a modified DNA polymerase gene in which TAC at positions 19 to 21 in SEQ ID NO: 12 was substituted with GCC, GTT at positions 277 to 279 in SEQ ID NO: 12 was substituted with AAA, and AAT at positions 628 to 630 in SEQ ID NO: 12 was substituted with GAC) was prepared in the same manner as in Production Example 2. pPfu Y7A/V93K was used as a template, and primers represented by SEQ ID NOs: 38 and 39 were used as mutagenesis primers. Further, a modified DNA polymerase (Pfu N210D/Y7A/V93K) was obtained by using the same purification method as in Production Example 2.

The modified DNA polymerases obtained in Production Examples 2 to 28 were subjected to the tests described below in Examples 1 to 6.

Example 1

Evaluation of Uracil Sensitivity of Modified DNA Polymerases

PCR was performed by the following method to evaluate uracil sensitivity. For PCR, components included in KOD-Plus-Ver. 2 (produced by Toyobo Co. Ltd.) were used. dUTP (produced by Roche) was added to 50 μl of individual reaction solutions containing 1×PCR buffer, 1.5 mM MgSO$_4$, dNTPs (dATP, dTTP, dCTP, dGTP) in an amount of 0.2 mM, primers represented by SEQ ID NOs: 25 and 26 in an amount of 15 pmol for amplifying about 1.3 kb, 10 ng of human genomic DNA (produced by Roche), and 1 U of each respective enzyme, to final concentrations of 0.5, 5, 50, 100, and 200 μM. PCR was performed using a GeneAmp PCR system 9700 (produced by Applied Biosystems) on the following schedule: preliminary reaction at 94° C. for 30 seconds, followed by 30 cycles, each cycle consisting of 98° C. for 10 seconds, 65° C. for 30 seconds, and 68° C. for 1 minute and 30 seconds. After the completion of each individual reaction, 5 μl of each of the resulting reaction solutions was subjected to agarose electrophoresis, followed by ethidium bromide staining. Under ultraviolet irradiation, amplified DNA fragments of about 1.3 kb were confirmed. FIGS. 3, 4, 7, and 8 show the results.

The results reveal that the wild-type DNA polymerase from *Thermococcus kodakaraensis* (KOD) was inhibited by the addition of 0.5 μM of dUTP, and no PCR products were confirmed, whereas in the mutants in which Y7A, P36H, P36K, P36R, V93Q, V93K, or V93R was introduced in the uracil binding pockets, PCR products were confirmed even when some amount of dUTP was added. In addition, a comparison of Y7A and P36K and P36K/Y7A shows that the double mutant was more tolerant of the addition of high concentration of dUTP and provided a larger amount of amplification, compared to the single mutants (FIGS. 3 and 4).

In Pfu, a comparison of Y7A and P36H single mutants and Y7A/P36H multiple mutant also shows similar results, i.e., the multiple mutant provided a larger amount of amplification.

Figure 4:
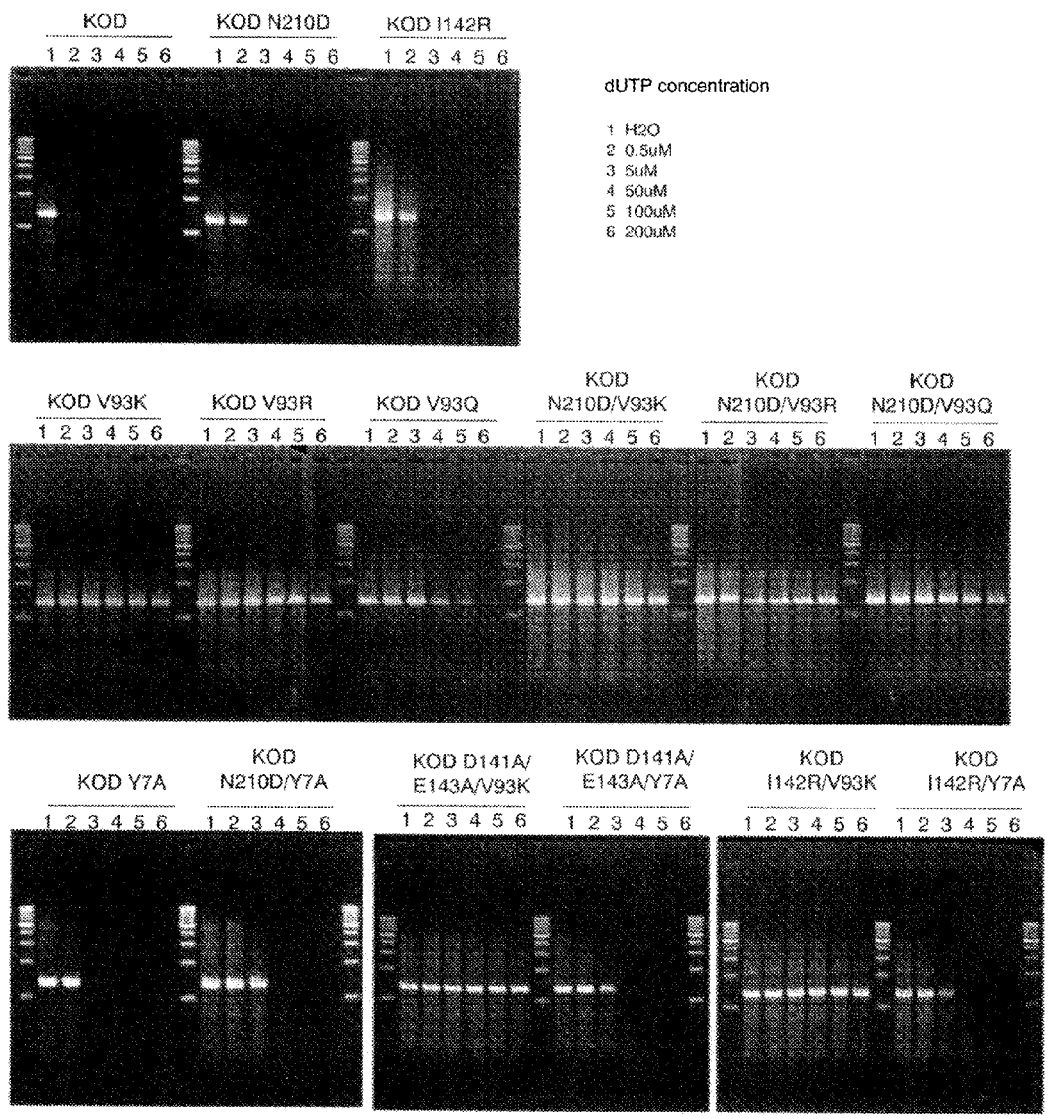
FIG. 4 illustrates amplification in PCR performed with the addition of dUTP to the reaction system to assess dUTP sensitivity.
Figure 7:
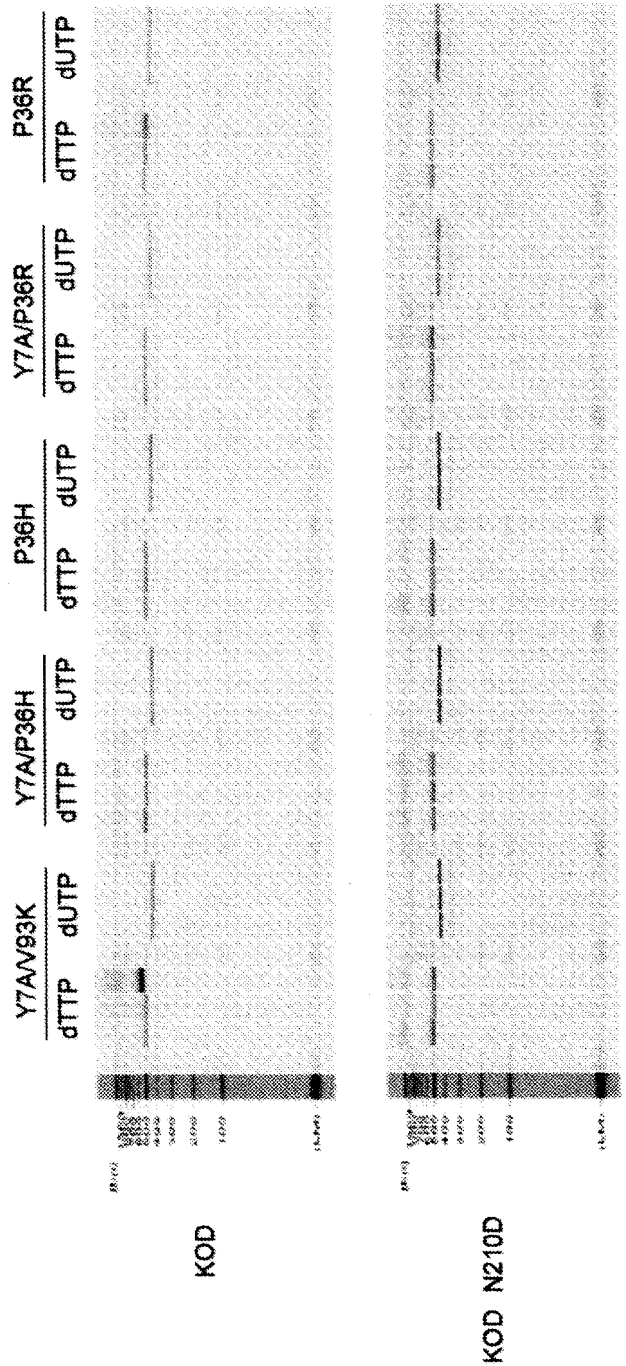
FIG. 7 illustrates PCR amplification of 482 bp in the presence of 100% dUTP.
Figure 8:
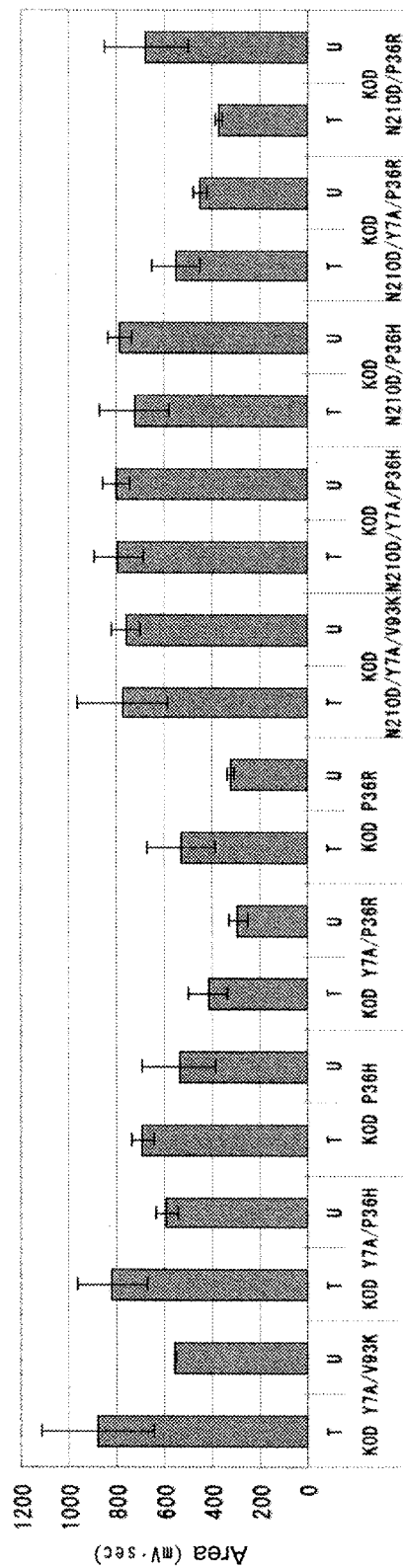
FIG. 8 illustrates the amounts of the PCR amplification in FIG. 7 as the electrophoresis peak area.

Additionally, it was confirmed that in KOD polymerase, N210D, D141A/E143A, or I142R exo(–) mutant was less sensitive to dUTP than the wild-type DNA polymerase, and when Y7A or a mutation at P36 or V93 position was introduced in the exo(–) mutants, the sensitivity to dUTP was further reduced (FIG. 4). This is presumably because when incorporating dUTP into DNA, the wild-type DNA polymerase exhibits a proofreading function to cleave dUTP with 3'-5' exonuclease, whereas the exo(–) mutants cannot cleave dUTP, thus allowing extension to continue. Accordingly, it is suggested that the amount of amplification is improved in PCR with dUTP when modification(s) that render exo activity deficient are introduced in addition to mutation(s) in the uracil binding pocket(s) (FIGS. 7 and 8).

Example 2

Figure 5:
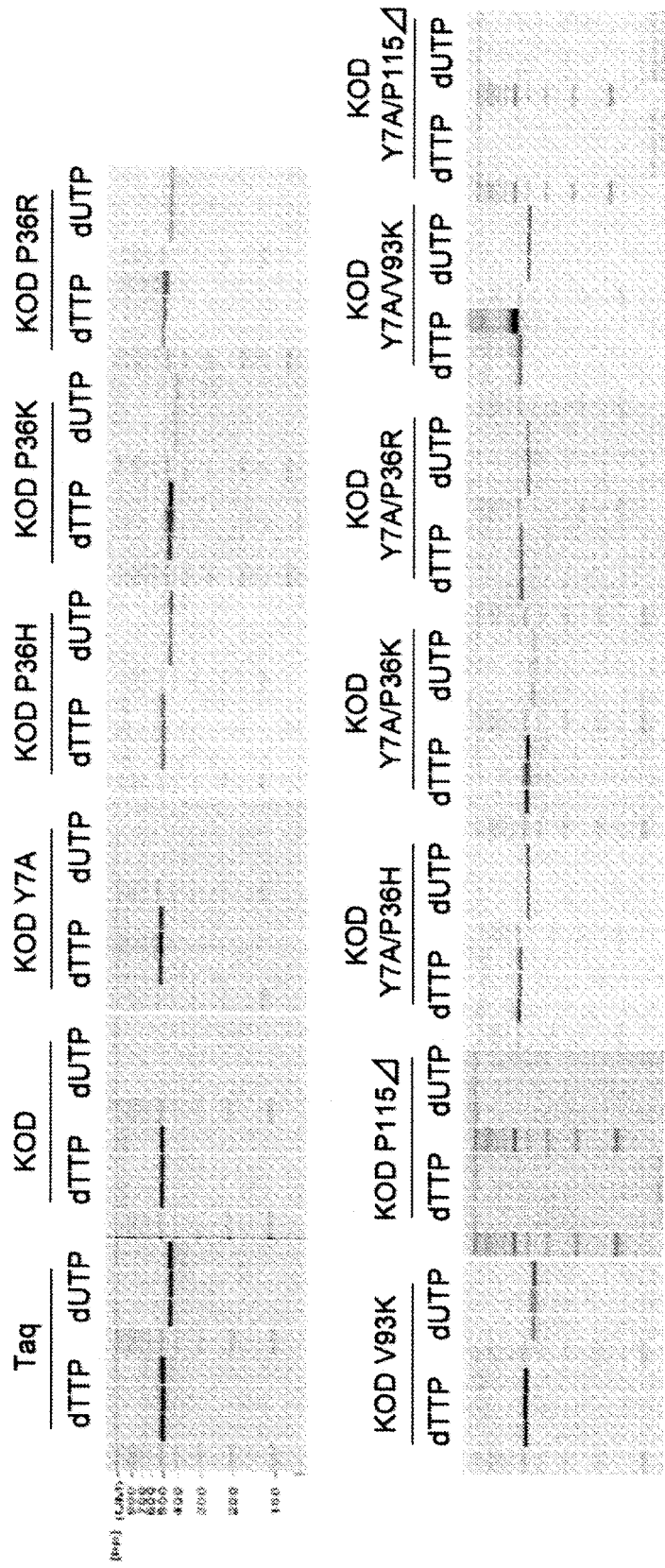
FIG. 5 illustrates PCR amplification of 482 bp in the presence of 100% dUTP.
Figure 6:
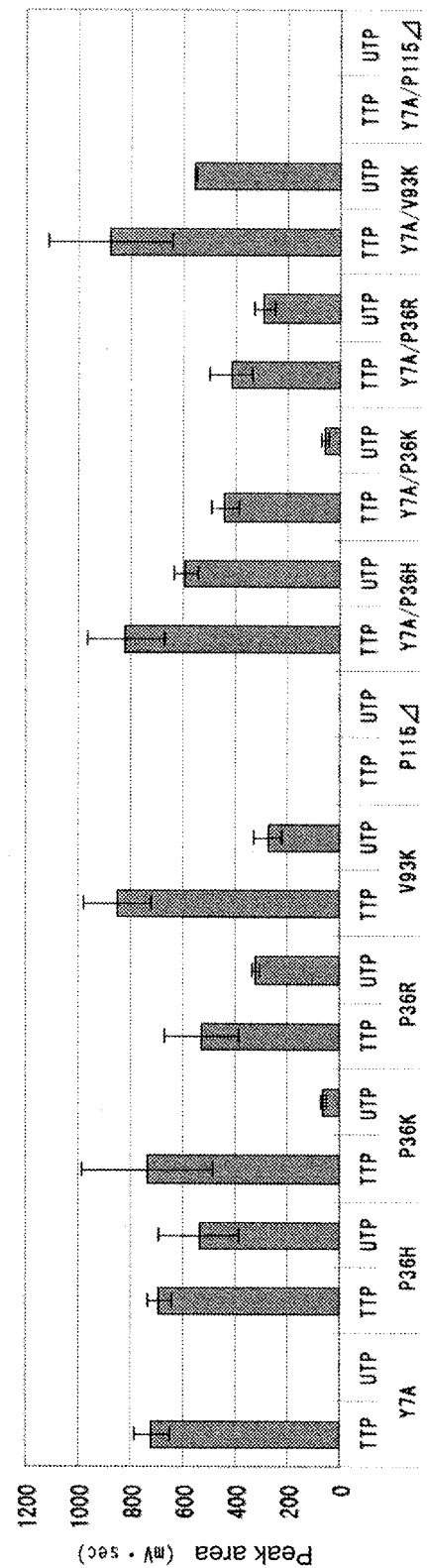
FIG. 6 illustrates the amounts of the PCR amplification in FIG. 5 as the electrophoresis peak area.

Evaluation of Amount of PCR Amplification Using Modified DNA Polymerases 482 bp of human β-globin was amplified to compare the amplification difference between the case of using dTTP and the case of using dUTP in PCR, and the sensitivity to dUTP was examined. For amplification, each enzyme was used after being mixed with 1 μg of a KOD antibody per U of the enzyme. For PCR, components included in KOD-Plus-Ver. 2 (produced by Toyobo Co. Ltd.) were used. General dNTPs (dATP, dTTP, dCTP, dGTP) in an amount of 0.2 mM were added to 50 μl of individual reaction solutions, and dNTPs (dATP, dUTP, dCTP, dGTP) in an amount of 0.2 mM in which dTTP was replaced by dUTP were added to 50 μl of individual reaction solutions. The reaction solutions contained 1× PCR buffer, 1.5 mM MgSO$_4$, primers represented by SEQ ID NOs: 27 and 28 in an amount of 15 pmol for amplifying 481 kb, 10 ng of human genomic DNA (produced by Roche), and 1 U of each respective enzyme mixed with the antibody. PCR was performed using a GeneAmp PCR system 9700 (produced by Applied Biosystems) on the following schedule: preliminary reaction at 94° C. for 2 minutes, followed by 35 cycles, each cycle consisting of 98° C. for 10 seconds and 68° C. for 1 minute. After the completion of each individual reaction, each of the resulting reaction solutions was analyzed using to a DNA-1000 kit for MultiNA (produced by Shimadzu Corporation) to confirm amplified DNA fragments. FIGS. 5 and 6 show the results.

The results reveal that the DNA was not PCR-amplified with Y7A single mutant, but a combination of Y7A with V93K, P36H, P36K, or P36R allowed for PCR amplification. In particular, a combination of V93K/Y7A is shown to greatly improve the amplification amount, compared to V93K (FIGS. 5 and 6).

In addition, the mutants obtained by introducing mutation(s) such as V93K/Y7A or P36H in the wild-type DNA polymerase and the mutants obtained by introducing mutation(s) such as V93K/Y7A or P36H in N210D exo(–) mutant were compared. The results show that the mutants obtained by introducing mutation(s) in the exo(–) DNA polymerase provided larger amounts of amplification. In the mutants obtained by introducing mutation(s) in the exo(–) DNA polymerase, almost no difference in the amplification amount between the case of using dUTP and the case of using dTTP was observed. This suggests that the sensitivity to dUTP is reduced and the amount of amplification is improved when mutation(s) are introduced in the exo regions in addition to mutation(s) in the uracil binding pockets(s) (FIGS. 7 and 8).

In Pfu, similar results were also obtained with the mutants obtained by introducing mutations Y7A/P36H or Y7A/V93K in N210D mutant.

Example 3

Evaluation of Amplification of Long-Chain DNA Using Modified DNA Polymerases

Figure 9:
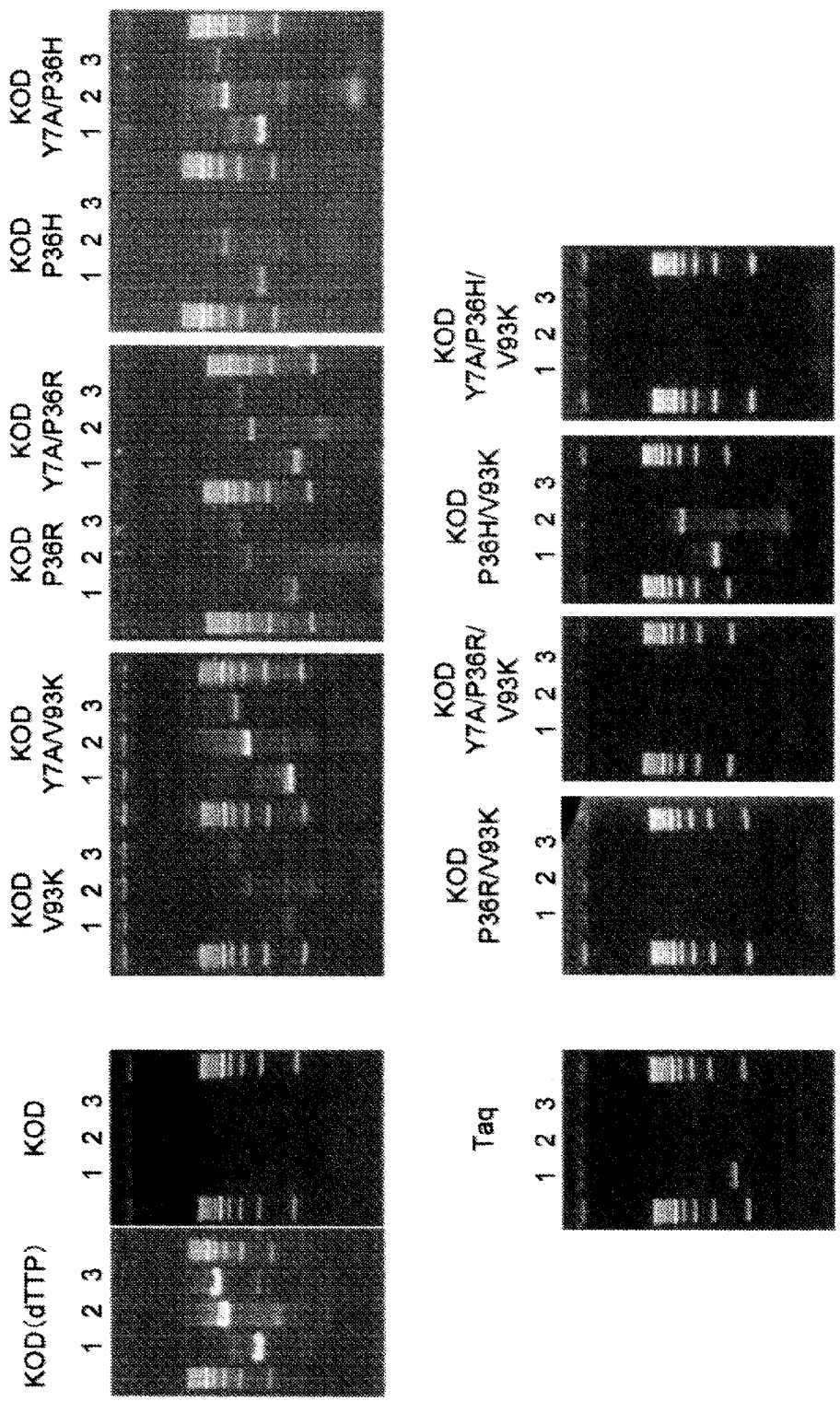
FIG. 9 illustrates PCR amplification of long-chain DNA in the presence of 100% dUTP.
Figure 10:
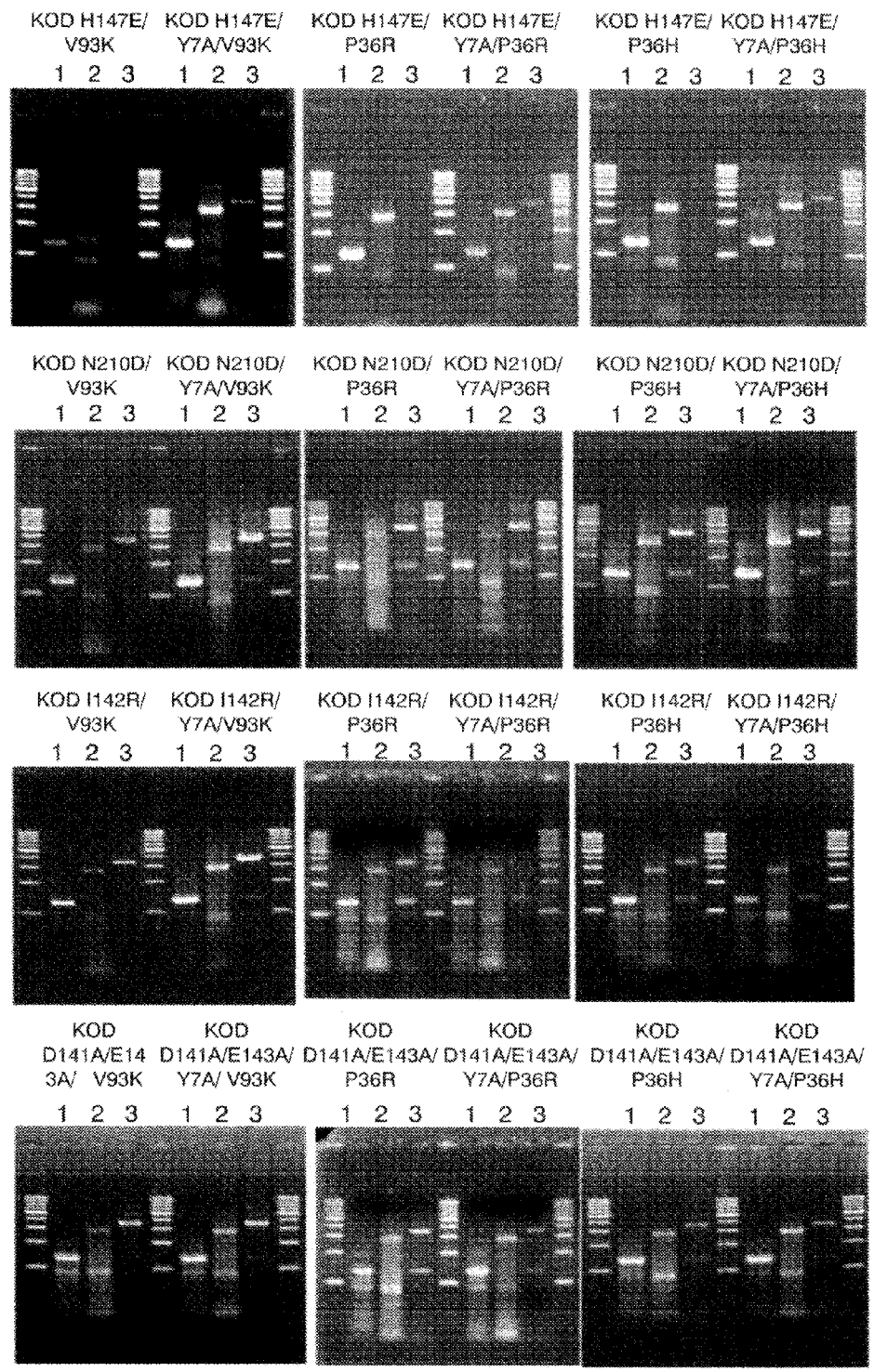
FIG. 10 illustrates PCR amplification of long-chain DNA in the presence of 100% dUTP.

Amplification of 1.3 kbp, 2.8 kbp, and 3.6 kbp of human β-globin in PCR using dUTP was compared. For amplification, each enzyme was used after being mixed with 1 μg of a KOD antibody per U of the enzyme. For PCR, components included in KOD-Plus-Ver. 2 (produced by Toyobo Co. Ltd.) were used. 50 μl of individual reaction solutions containing 1×PCR buffer, 1.5 mM MgSO$_4$, dNTPs (dATP, dUTP, dCTP, dGTP) in an amount of 2 mM in which dTTP was replaced by dUTP, primers in an amount of 15 pmol (SEQ ID NOs: 25 and 26 for amplification of 1.3 kbp; SEQ ID NOs: 26 and 29 for amplification of 2.8 kbp; SEQ ID NOs: 30 and 31 for amplification of 3.6 kbp), 10 ng of human genomic DNA (produced by Roche), and 1 U of each respective enzyme mixed with the antibody were used. PCR was performed using a GeneAmp PCR system 9700 (Applied Biosystems) on the following schedule: preliminary reaction at 94° C. for 2 minutes, followed by 35 cycles, each cycle consisting of 98° C. for 10 seconds, 65° C. for 30 seconds, and 68° C. for about 1 minute per kbp (1 minute and 30 seconds for amplification of 1.3 kbp; 3 minutes for amplification of 2.8 kbp; 4 minutes for amplification of 3.6 kbp). As a control, amplification was also performed using Taq DNA polymerase. Taq DNA polymerase produced by Toyobo Co. Ltd. mixed with Anti-Taq High (produced by Toyobo Co. Ltd.) was used. 50 μl of a reaction solution containing 1× buffer included in Blend Taq, dNTPs (dATP, dUTP, dCTP, dGTP) in an amount of 2 mM in which dTTP was replaced by dUTP, primers in an amount of 10 pmol the same as the above), 10 ng of human genomic DNA (produced by Roche), and 2.5 U of the enzyme mixed with the antibody was used. PCR was performed using a GeneAmp PCR system 9700 (produced by Applied Biosystems) on the following schedule: preliminary reaction at 94° C. for 2 minutes, followed by 35 cycles, each cycle consisting of 94° C. for 30 seconds, 65° C. for 30 seconds, and 68° C. for about 1 minute per kbp (1 minute and 30 seconds for amplification of 1.3 kbp; 3 minutes for amplification of 2.8 kbp; 4 minutes for amplification of 3.6 kbp). After the completion of each individual reaction, 5 μl of each of the resulting reaction solutions was subjected to agarose electrophoresis, followed by ethidium bromide staining, and the amount of amplified DNA fragments was confirmed under ultraviolet irradiation. FIGS. 9 and 10 show the results.

The amounts of amplification were compared between V93K and Y7A/V93K, P93H and Y7A/P36H, P36R and Y7A/P36R, and P36H or V93K and P36H/V93K. The results confirm that the mutants obtained by introducing a mutation at P36 position provided larger amounts of amplification and amplified a longer target, compared to V93K mutant. Additionally, the mutants obtained by introducing double mutations in the uracil binding pocket(s) provided larger amounts of amplification than the single mutants. These mutants allowed amplification of long chain length, which cannot be amplified by using Taq (FIG. 9). In addition, the mutants obtained by introducing mutation(s) such as V93K or P36H in the wild-type DNA polymerase and the mutants obtained by introducing mutation(s) such as V93K or P36H in N210D, I142R, or D141A/E143A exo(−) mutant were compared. The results show that the mutants obtained by introducing mutation(s) in the exo(−) DNA polymerases provided larger amounts of amplification (FIG. 10). Further, a comparison of the mutants obtained by introducing mutation(s) such as V93K or P36H in the wild-type DNA polymerase and the mutants obtained by introducing mutation(s) such as V93K or P36H in H147E mutant, a mutant that improves PCR efficiency shows that H147E mutants provided larger amounts of amplification. This is presumably because the effect of modification H147E is obtained independently of modification to the uracil binding pocket(s), and the amount of amplification is increased by the effect of modification H147E.

Table 1 shows the results of Examples 1 to 3. In Table 1, evaluation of dUTP resistance on an 11-point scale indicates that the closer to 0 the value, the stronger the sensitivity to dUTP, and the closer to 10 the value, the lower the sensitivity to dUTP. In Table 1, "A" indicates sufficient amplification, "B" indicates a certain degree of amplification, and "C" indicates no amplification.

TABLE 1

| Amino acid in exo regions | Amino acid involved in uracil binging | Evaluation of dUTP resisitance on a 11-point scale | dUTP resistance (μM) | Results of PCR in the presence of dUTP | | | |
|---|---|---|---|---|---|---|---|
| | | | | 481 bp | 1.3 kbp | 2.8 kbp | 3.6 kbp |
| − | Y7A | 2 | 0.5 | C | C | C | C |
| | P36H | 5 | >200 | A | B | B | C |
| | P36K | 3 | 100 | A | N.D. | N.D. | N.D. |
| | P36R | 5 | >200 | A | B | B | B |
| | V93Q | 3 | 100 | A | C | C | C |
| | V93K | 6 | >200 | A | B | B | B |
| | V93R | 5 | >200 | A | B | B | B |
| | P115Δ | 0 | 0 | C | C | C | C |
| | Y7A/P36H | 8 | >200 | A | A | A | B |
| | Y7A/P36R | 7 | >200 | A | A | A | B |
| | Y7A/V93K | 8 | >200 | A | A | A | B |
| | Y7A/P115Δ | 0 | 0 | C | C | C | C |
| | P36H/V93K | 7 | >200 | A | A | A | C |
| | P36R/V93K | 0 | 0 | C | C | C | C |
| | Y7A/P36H/V93K | 0 | N.D. | C | C | C | C |
| | Y7A/P36R/V93K | 0 | N.D. | C | C | C | C |
| H147E (exo (+)) | Y7A | 2 | 0.5 | C | C | C | C |
| | P36H | 6 | >200 | A | B | B | C |
| | P36K | 4 | 100 | A | N.D. | N.D. | N.D. |
| | P36R | 6 | >200 | A | B | B | B |
| | V93Q | 4 | 100 | A | C | C | C |
| | V93K | 6 | >200 | A | B | B | B |
| | V93R | 6 | >200 | A | B | B | B |
| | P115Δ | 0 | 0 | C | C | C | C |
| | Y7A/P36H | 8 | >200 | A | A | A | B |
| | Y7A/P36R | 8 | >200 | A | A | A | B |
| | Y7A/V93K | 8 | >200 | A | A | A | B |
| | Y7A/P115Δ | 0 | 0 | C | C | C | C |
| | P36H/V93K | 8 | >200 | A | A | A | C |
| | P36R/V93K | 0 | 0 | C | C | C | C |
| | Y7A/P36H/V93K | 0 | N.D. | C | C | C | C |
| | Y7A/P36R/V93K | 0 | N.D. | C | C | C | C |

TABLE 1-continued

| Amino acid in exo regions | Amino acid involved in uracil binging | Evaluation of dUTP resisitance on a 11-point scale | dUTP resistance (µM) | Results of PCR in the presence of dUTP | | | |
|---|---|---|---|---|---|---|---|
| | | | | 481 bp | 1.3 kbp | 2.8 kbp | 3.6 kbp |
| N210D (exo (−)) | Y7A | 2 | 5 | C | C | C | C |
| | P36H | 8 | >200 | A | A | A | A |
| | P36K | 8 | >200 | A | N.D. | N.D. | N.D. |
| | P36R | 8 | >200 | A | A | A | A |
| | V93Q | 6 | >200 | A | C | C | C |
| | V93K | 8 | >200 | A | A | B | B |
| | V93R | 8 | >200 | A | A | B | B |
| | P115Δ | 0 | 0 | C | C | C | C |
| | Y7A/P36H | 10 | >200 | A | A | A | A |
| | Y7A/P36R | 10 | >200 | A | A | A | A |
| | Y7A/V93K | 10 | >200 | A | A | A | A |
| | Y7A/P115Δ | 0 | 0 | C | C | C | C |
| I142R (exo (−)) | Y7A | 2 | 5 | C | C | C | C |
| | V93K | 8 | >200 | A | A | B | B |
| | Y7A/V93K | 10 | >200 | A | A | A | A |
| | P36H | 8 | >200 | A | A | A | A |
| | P36R | 8 | >200 | A | A | A | A |
| | Y7A/P36H | 8 | >200 | A | A | A | C |
| | Y7A/P36R | 8 | >200 | A | A | A | B |
| D141A/E143A (exo (−)) | Y7A | 2 | 5 | C | C | C | C |
| | V93K | 8 | >200 | A | A | B | B |
| | Y7A/V93K | 10 | >200 | A | A | A | A |
| | P36H | 8 | >200 | A | A | A | A |
| | P36R | 8 | >200 | A | A | A | A |
| | Y7A/P36H | 10 | >200 | A | A | A | A |
| | Y7A/P36R | 10 | >200 | A | A | A | A |

A: Amplified
B: Amplified (faint band)
C: Not amplified

In Pfu as well, a comparison of Y7A, P36H, and V93K single mutants and Y7A/P36H and Y7A/V93K multiple mutants shows similar results, i.e., the multiple mutants provided larger amounts of amplification.

In addition, the mutants obtained by introducing mutation(s) in the uracil binding pocket(s) of the wild-type DNA polymerase and the mutants obtained by introducing mutation(s) in the uracil binding pocket(s) of N210D exo(−) mutant were compared. The results show that the mutants obtained by introducing mutation(s) in the exo(−) DNA polymerase provided larger amounts of amplification. In Pfu, similar results were also obtained with the mutants obtained by introducing mutations Y7A/P36H or Y7A/V93K in N210D mutant.

Example 4

Comparison of Amplification Using Inosine-Containing Primers

Using inosine-containing primers, the difference in PCR amplification was compared. For comparison, KOD mutants and KOD (wild-type), each mixed with 1 µg of a KOD antibody per U of the enzyme, and Taq DNA polymerase mixed with an antibody (a mixture of equal amounts of Taq DNA polymerase (produced by Toyobo Co. Ltd.) and Anti-Taq High (produced by Toyobo Co. Ltd.)) were used.

For PCR with the KOD mutants and PCR with the KOD, a buffer, MgSO₄, and dNTPs included in KOD-Plus-Ver. 2 (produced by Toyobo Co. Ltd.) were used. 50 µl of individual reaction solutions containing 1×PCR buffer, 1.5 mM MgSO₄, dNTPs (dATP, dTTP, dCTP, dGTP) in an amount of 0.2 mM, primers (SEQ ID NOs: 40 and 41) in an amount of 75 pmol or 150 pmol, 100 ng of *Psychrobacter* DNA, and 1 U of each respective enzyme mixed with the antibody were used. PCR was performed using a GeneAmp PCR system 9700 (Applied Biosystems) on the following schedule: preliminary reaction at 94° C. for 2 minutes, followed by 35 cycles, each cycle consisting of 98° C. for 10 seconds, 54° C. for 10 seconds, and 68° C. for 1 minute.

For PCR with the Taq DNA polymerase, 50 µl of a reaction solution containing 1× buffer included in Blend Taq (product of Toyobo), dNTPs (dATP, dUTP, dCTP, dGTP) in an amount of 0.2 mM, primers in an amount of 75 pmol or 150 pmol (the same as above), 100 ng of *Psychrobacter* DNA, and 2.5 U of the enzyme mixed with the antibody was used. PCR was performed using a GeneAmp PCR system 9700 (Applied Biosystems) on the following schedule: preliminary reaction at 94° C. for 2 minutes, followed by 35 cycles, each cycle consisting of 94° C. for 30 seconds, 54° C. for 30 seconds, and 68° C. for 1 minute.

Figure 11:
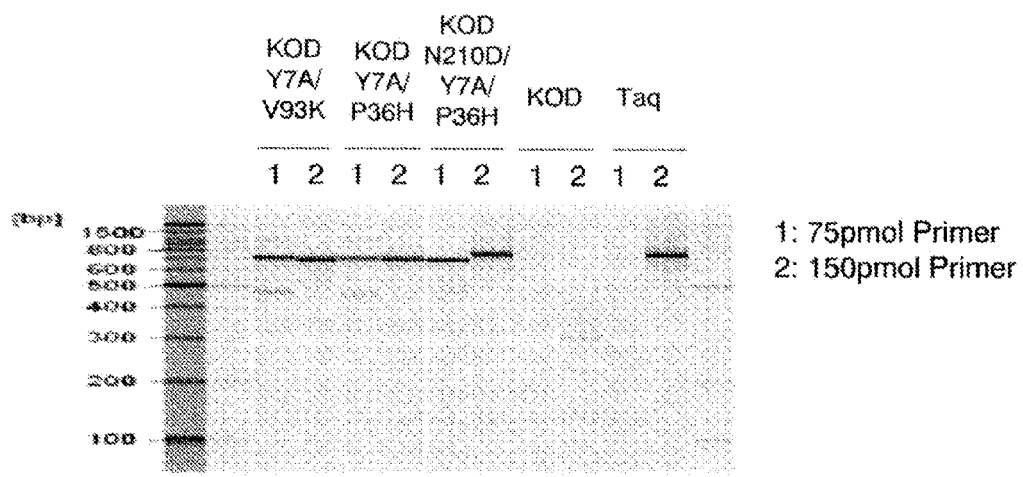
FIG. 11 illustrates amplification in PCR performed using inosine-containing primers.

After the completion of each individual reaction, each of the resulting reaction solutions was analyzed using a DNA-1000 kit for MultiNA (produced by Shimadzu Corporation) to confirm amplified DNA fragments. FIG. 11 shows the results.

The results reveal that the DNA was not amplified with the inosine-containing primers by using the KOD (wild-type), whereas stable amplification was confirmed in the KOD mutants (Y7A/V93K, V7A/P36H, and N210D/Y7A/P36H) and the Taq DNA polymerase (FIG. 11). This shows that the mutants with low uracil sensitivity are also less sensitive to inosine. Since KOD has higher fidelity than that of Taq DNA polymerase, it allows for amplification without introducing errors into the amplification products. High fidelity is very important in cloning; therefore, the KOD mutants are considered superior to the Taq DNA polymerase. Additionally, no amplification was observed in the Taq DNA polymerase unless primers in an amount of 150 pmol were added, whereas amplification was observed in the KOD mutants with the addition of primers in an amount of 75 pmol. This indicates that the KOD mutants have better amplification efficiency.

Example 5

Comparison of Amplification of Bisulfite-Treated DNA

Using bisulfite-treated DNA as a template and various primers, the difference in PCR amplification was compared. For comparison, KOD mutant (Y7A/V93K) and KOD (wild-type), each mixed with 1 μg of a KOD antibody per U of the enzyme, and Taq DNA polymerase mixed with an antibody (a mixture of equal amounts of Taq DNA polymerase (produced by Toyobo Co. Ltd.) and Anti-Taq High (produced by Toyobo Co. Ltd.)) were used.

The bisulfite-treated DNA used was human genomic DNA (produced by Roche) that had been treated with a MethylCode Bisulfite Conversion Kit of Invitrogen.

For PCR with the KOD mutant (Y7A/V93K) and PCR with the KOD, a buffer, MgSO$_4$, and dNTPs included in KOD-Plus-Ver. 2 (produced by Toyobo Co. Ltd.) were used. 50 μl of individual reaction solutions containing 1×PCR buffer, 1.5 mM MgSO$_4$, dNTPs (dATP, dTTP, dCTP, dGTP) in an amount of 0.2 mM, primers (SEQ ID NOs: 42 and 43 for amplification of MINT1; SEQ ID NOs: 44 and 45 for amplification of RAR; SEQ ID NOs: 46 and 47 for amplification of THBS1; SEQ ID NOs: 48 and 49 for amplification of MINT31) in an amount of 15 pmol, 1 μl of bisulfite-treated DNA extract, and 1 U of each respective enzyme mixed with the antibody were used. PCR was performed using a GeneAmp PCR system 9700 (Applied Biosystems) on the following schedule: preliminary reaction at 94° C. for 2 minutes, followed by 40 cycles, each cycle consisting of 98° C. for 10 seconds, 55° C. for 15 seconds, and 68° C. for 1 minute.

For PCR with the Taq DNA polymerase, 50 μl of a reaction solution containing 1× buffer included in Blend Taq (product of Toyobo), dNTPs (dATP, dUTP, dCTP, dGTP) in an amount of 0.2 mM, primers in an amount of 15 pmol (the same as above), 1 μl of bisulfite-treated DNA extract, and 2.5 U of the enzyme mixed with the antibody was used. PCR was performed using a GeneAmp PCR system 9700 (Applied Biosystems) on the following schedule: preliminary reaction at 94° C. for 2 minutes, followed by 40 cycles, each cycle consisting of 94° C. for 30 seconds, 55° C. for 30 seconds, and 68° C. for 1 minute.

Figure 12:
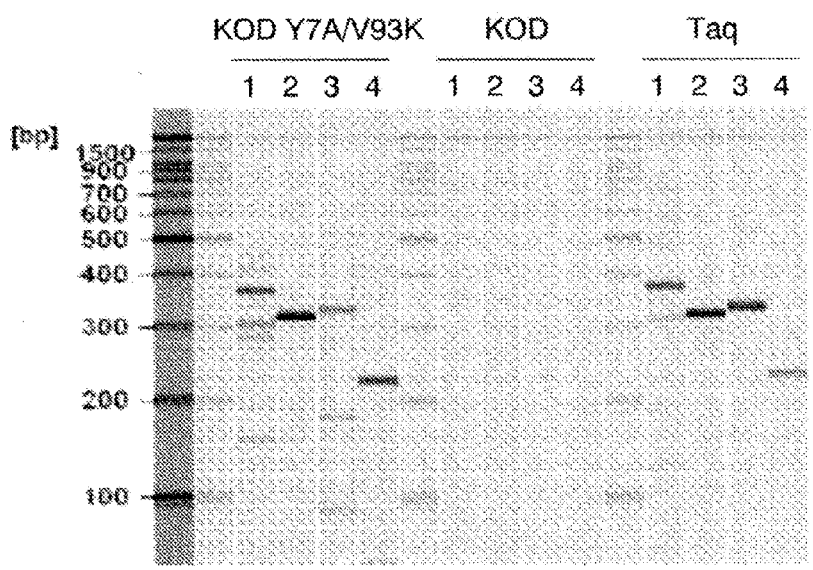
FIG. 12 illustrates amplification in PCR performed using bisulfite-treated DNA.

After the completion of each individual reaction, each of the resulting reaction solutions was analyzed using a DNA-1000 kit for MultiNA (produced by Shimadzu Corporation) to confirm amplified DNA fragments. FIG. 12 shows the results.

The results reveal that the bisulfite-treated DNA was not amplified with the KOD (wild-type), whereas stable amplification was confirmed in KOD Y7A/V93K and the Taq DNA polymerase (FIG. 12).

In the same manner as in KOD Y7A/V93K mutant, similar results were also obtained in KOD Y7A/P36H mutant, KOD N210D Y7A/P36H mutant, and Pfu Y7A/V93K mutant. This shows that even if the template contains uracil, the mutants with low uracil sensitivity allow for amplification, and the mutants with low uracil sensitivity allow for amplification, even with bisulfite-treated DNA.

Example 6

Confirmation of Degradation with UNG of DNA Amplified in the Presence of dUTP

Figure 13:
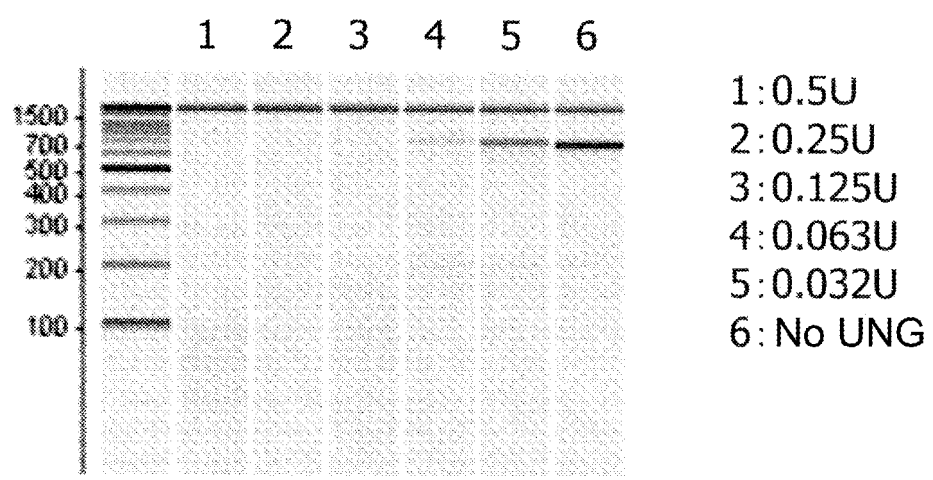
FIG. 13 illustrates degradation, with UNG, of PCR products amplified in the presence of dUTP.

It was confirmed whether 0.7 kbp of human β-globin amplified using KOD mutant with reduced uracil sensitivity (N210D/Y7A/P36H) in PCR with dUTP was degraded by being reacted with UNG. For PCR, components included in KOD-Plus-Ver. 2 (produced by Toyobo Co. Ltd.) were used. 50 μl of a reaction solution containing 1×PCR buffer, 1.5 mM MgSO$_4$, dNTPs (dATP, dUTP, dCTP, dGTP) in an amount of 2 mM in which dTTP was replaced by dUTP, primers (SEQ ID NOs: 50 and 51) in an amount of 15 pmol, 10 ng of human genomic DNA (produced by Roche), and 1 U of the enzyme mixed with an antibody was used. PCR was performed using a GeneAmp PCR system 9700 (Applied Biosystems) on the following schedule: preliminary reaction at 94° C. for 2 minutes, followed by 35 cycles, each cycle consisting of 98° C. for 10 seconds, 60° C. for 30 seconds, and 68° C. for 1 minute. The amplification products were diluted with the above-mentioned 1×PCR buffer to 10 ng/μl, 8 μl of the diluted amplification products was mixed with 2 μl of various concentrations of UNG (produced by Roche), and the mixtures were reacted at 37° C. for 10 minutes. After the completion of each individual reaction, each of the mixtures was analyzed using a DNA-1000 kit for MultiNA (produced by Shimadzu Corporation) to confirm the amount of amplification products. FIG. 13 shows the results.

The results confirm that 80 ng of DNA was completely degraded with 0.25 U of UNG. This shows that even DNA amplified using the KOD mutant with reduced uracil sensitivity (N210D/Y7A/P36H) can be degraded by being reacted with UNG (FIG. 13).

In DNA amplified using other mutants (KOD Y7A/V93K, Pfu Y7A/V93K, KOD Y7A/P36H), similar results, such that the DNA was degraded with UNG in the same manner as above, were also obtained.

INDUSTRIAL APPLICABILITY

The present invention allows Archaea-derived DNA polymerases belonging to family B to sufficiently exhibit amplification efficiency. The present invention also enables the use of dUTP/UNG decontamination methods with Archaea-derived DNA polymerases belonging to family B. High fidelity and resistance to impurities of DNA polymerases belonging to family B allow them to be widely used in the research field, the field of forensic medicine, such as in genetic diagnosis, and, for example, in testing for microorganisms in foods and the environment.

The invention claimed is:

1. A modified DNA polymerase, comprising:
the amino acid sequence of SEQ ID NO: 1, except that at least one amino acid in a position corresponding to position 7, 36, 37, 90-97, 112-119, 137-147, 206-222 and 308-318 is modified,
wherein the amino acid sequence includes two amino acid substitutions selected from (a) to (c) below:
(a) Y7A,
(b) P36H, P36R, or P36K, and
(c) V93K, V93Q, V93R, or V93H.

2. The modified DNA polymerase according to claim 1, further comprising a modification of at least one amino acid selected from the group consisting of amino acids corresponding to D141, I142, E143, H147, and N210 in SEQ ID NO: 1.

3. The modified DNA polymerase according to claim 2, comprising at least one amino acid substitution selected from (d) to (g) below:
(d) D141A and E143A,
(e) I142R,
(f) N210D, and
(g) H147E or H147D.

4. A method for amplifying nucleic acids, comprising using the modified DNA polymerase according to claim 1.

5. The method according to claim 4, comprising using inosine-containing primers.

6. The method according to claim 4, comprising using bisulfate-treated DNA as a template.

7. A reagent for amplifying nucleic acids, comprising the modified DNA polymerase according to claim 1.

8. A kit comprising the reagent according to claim 7.

9. A modified DNA polymerase, comprising:
the amino acid sequence of SEQ ID NO: 1, except that an amino acid in a position corresponding to position 36 is modified,
wherein the amino acid sequence includes a P36H, P36R, or P36K amino acid substitution.

10. The modified DNA polymerase according to claim 1, wherein the modified DNA polymerase comprises the amino acid sequence of SEQ ID NO: 1, except that the sequence includes the following amino acids substitutions:
Y7A and P36H; or
Y7A and V93K.

11. The modified DNA polymerase according to claim 1, wherein the modified DNA polymerase comprises the following amino acid substitutions:
Y7A and P36H; or
Y7A and V93K.

12. The modified DNA polymerase according to claim 9, wherein the modification at position 36 is P36H.

13. The modified DNA polymerase according to claim 1, wherein the modified DNA polymerase comprises the amino acid sequence of SEQ ID NO: 1, except that the sequence includes the following amino acids substitutions:
Y7A and P36H.

14. The modified DNA polymerase according to claim 1, wherein the modified DNA polymerase comprises the following amino acid substitutions:
Y7A and P36H.

15. The modified DNA polymerase according to claim 1, wherein the modified DNA polymerase comprises the amino acid sequence of SEQ ID NO: 1, except that the sequence includes the following amino acids substitutions:
Y7A and V93Q.

16. The modified DNA polymerase according to claim 1, wherein the modified DNA polymerase comprises the following amino acid substitutions:
Y7A and V93Q.

* * * * *

SEQUENCE LISTING

<160> NUMBER OF SEQ ID NOS: 51

<210> SEQ ID NO 1
<211> LENGTH: 774
<212> TYPE: PRT

<213> ORGANISM: Thermococcus kodakaraensis

<400> SEQUENCE: 1

```
Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Glu Tyr Asp Arg
            20                  25                  30
Thr Phe Glu Pro Tyr Phe Tyr Ala Leu Leu Lys Asp Asp Ser Ala Ile
        35                  40                  45
Glu Glu Val Lys Lys Ile Thr Ala Glu Arg His Gly Thr Val Val Thr
    50                  55                  60
Val Lys Arg Val Glu Lys Val Gln Lys Lys Phe Leu Gly Arg Pro Val
65                  70                  75                  80
Glu Val Trp Lys Leu Tyr Phe Thr His Pro Gln Asp Val Pro Ala Ile
                85                  90                  95
Arg Asp Lys Ile Arg Glu His Pro Ala Val Ile Asp Ile Tyr Glu Tyr
            100                 105                 110
Asp Ile Pro Phe Ala Lys Arg Tyr Leu Ile Asp Lys Gly Leu Val Pro
        115                 120                 125
Met Glu Gly Asp Glu Glu Leu Lys Met Leu Ala Phe Asp Ile Glu Thr
    130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Val
                165                 170                 175
Asp Leu Pro Tyr Val Asp Val Val Ser Thr Glu Arg Glu Met Ile Lys
            180                 185                 190
Arg Phe Leu Arg Val Val Lys Glu Lys Asp Pro Asp Val Leu Ile Thr
        195                 200                 205
Tyr Asn Gly Asp Asn Phe Asp Phe Ala Tyr Leu Lys Lys Arg Cys Glu
    210                 215                 220
Lys Leu Gly Ile Asn Phe Ala Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Gln Pro Lys Glu
        275                 280                 285
Lys Val Tyr Ala Glu Glu Ile Thr Thr Ala Trp Glu Thr Gly Glu Asn
    290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Lys Glu Leu Ala Arg Arg Gln Ser Tyr
    370                 375                 380
Glu Gly Gly Tyr Val Lys Glu Pro Glu Arg Gly Leu Trp Glu Asn Ile
385                 390                 395                 400
```

```
Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 2
<211> LENGTH: 775
<212> TYPE: PRT
<213> ORGANISM: Pyrococcus furiosus

<400> SEQUENCE: 2
```

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
            85                  90                  95

Arg Glu Lys Val Arg Glu His Pro Ala Val Val Asp Ile Phe Glu Tyr
        100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
        165                 170                 175

Asp Leu Pro Tyr Val Glu Val Ser Ser Glu Arg Glu Met Ile Lys
        180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Thr Arg Thr Ile Asn Leu Pro Thr
        260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
        290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
        325                 330                 335

Val Gly Gln Pro Leu Trp Asp Val Ser Arg Ser Ser Thr Gly Asn Leu
        340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
        370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415
```

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
            485                 490                 495

Tyr Tyr Gly Tyr Ala Lys Ala Arg Trp Tyr Cys Lys Glu Cys Ala Glu
        500                 505                 510

Ser Val Thr Ala Trp Gly Arg Lys Tyr Ile Glu Leu Val Trp Lys Glu
    515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
            565                 570                 575

Glu Leu Glu Tyr Glu Gly Phe Tyr Lys Arg Gly Phe Phe Val Thr Lys
        580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
            645                 650                 655

Pro Pro Glu Lys Leu Ala Ile Tyr Glu Gln Ile Thr Arg Pro Leu His
        660                 665                 670

Glu Tyr Lys Ala Ile Gly Pro His Val Ala Val Ala Lys Lys Leu Ala
    675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
        740                 745                 750

Lys Glu Asp Leu Arg Tyr Gln Lys Thr Arg Gln Val Gly Leu Thr Ser
    755                 760                 765

Trp Leu Asn Ile Lys Lys Ser
770                 775

<210> SEQ ID NO 3
<211> LENGTH: 773
<212> TYPE: PRT
<213> ORGANISM: Thermococcus gorgonarius

<400> SEQUENCE: 3

Met Ile Leu Asp Thr Asp Tyr Ile Thr Glu Asp Gly Lys Pro Val Ile
1               5                   10                  15

```
Arg Ile Phe Lys Lys Glu Asn Gly Glu Phe Lys Ile Asp Tyr Asp Arg
         20                  25                  30

Asn Phe Glu Pro Tyr Ile Tyr Ala Leu Leu Lys Asp Asp Ser Ala Ile
             35                  40                  45

Glu Asp Val Lys Lys Ile Thr Ala Glu Arg His Gly Thr Thr Val Arg
 50                  55                  60

Val Val Arg Ala Glu Lys Val Lys Lys Phe Leu Gly Arg Pro Ile
 65                  70                  75                  80

Glu Val Trp Lys Leu Tyr Phe Thr His Pro Gln Asp Val Pro Ala Ile
             85                  90                  95

Arg Asp Lys Ile Lys Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
             115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
             180                 185                 190

Arg Phe Leu Lys Val Val Lys Glu Lys Asp Pro Asp Val Leu Ile Thr
         195                 200                 205

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
             260                 265                 270

Tyr Thr Leu Glu Ala Val Tyr Glu Ala Ile Phe Gly Gln Pro Lys Glu
         275                 280                 285

Lys Val Tyr Ala Glu Glu Ile Ala Gln Ala Trp Glu Thr Gly Glu Gly
290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
             340                 345                 350

Val Glu Trp Phe Leu Leu Arg Lys Ala Tyr Glu Arg Asn Glu Leu Ala
         355                 360                 365

Pro Asn Lys Pro Asp Glu Arg Glu Leu Ala Arg Arg Arg Glu Ser Tyr
370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
             420                 425                 430
```

```
Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
450                 455                 460

Lys Lys Met Lys Ala Thr Ile Asp Pro Ile Glu Lys Lys Leu Leu Asp
465                 470                 475                 480

Tyr Arg Gln Arg Ala Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
            515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
            565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
            755                 760                 765

Leu Lys Pro Lys Thr
770

<210> SEQ ID NO 4
<211> LENGTH: 774
<212> TYPE: PRT
<213> ORGANISM: Thermococcus litoralis

<400> SEQUENCE: 4

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30
```

```
-continued

His Phe Gln Pro Tyr Ile Tyr Ala Leu Leu Lys Asp Asp Ser Ala Ile
            35                  40                  45

Glu Glu Ile Lys Ala Ile Lys Gly Glu Arg His Gly Lys Thr Val Arg
 50                  55                  60

Val Leu Asp Ala Val Lys Val Arg Lys Lys Phe Leu Gly Arg Glu Val
 65                  70                  75                  80

Glu Val Trp Lys Leu Ile Phe Glu His Pro Gln Asp Val Pro Ala Met
                 85                  90                  95

Arg Gly Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
            195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
            275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
            355                 360                 365

Leu Ala Pro Asn Lys Pro Asp Glu Glu Glu Tyr Lys Arg Arg Leu Arg
370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
            435                 440                 445
```

```
Pro Gly Phe Ile Pro Ser Ile Leu Gly Asp Leu Ile Ala Met Arg Gln
        450                 455                 460
Asp Ile Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
                485                 490                 495
Tyr Gly Tyr Met Gly Tyr Pro Lys Ala Arg Trp Tyr Ser Lys Glu Cys
                500                 505                 510
Ala Glu Ser Val Thr Ala Trp Gly Arg His Tyr Ile Glu Met Thr Ile
                515                 520                 525
Arg Glu Ile Glu Glu Lys Phe Gly Phe Lys Val Leu Tyr Ala Asp Thr
530                 535                 540
Asp Gly Phe Tyr Ala Thr Ile Pro Gly Glu Lys Pro Glu Leu Ile Lys
545                 550                 555                 560
Lys Lys Ala Lys Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
                580                 585                 590
Thr Lys Lys Arg Tyr Ala Val Ile Asp Glu Glu Gly Arg Ile Thr Thr
                595                 600                 605
Arg Gly Leu Glu Val Val Arg Arg Asp Trp Ser Glu Ile Ala Lys Glu
610                 615                 620
Thr Gln Ala Lys Val Leu Glu Ala Ile Leu Lys Glu Gly Ser Val Glu
625                 630                 635                 640
Lys Ala Val Glu Val Val Arg Asp Val Val Glu Lys Ile Ala Lys Tyr
                645                 650                 655
Arg Val Pro Leu Glu Lys Leu Val Ile His Glu Gln Ile Thr Arg Asp
                660                 665                 670
Leu Lys Asp Tyr Lys Ala Ile Gly Pro His Val Ala Ile Ala Lys Arg
                675                 680                 685
Leu Ala Ala Arg Gly Ile Lys Val Lys Pro Gly Thr Ile Ile Ser Tyr
                690                 695                 700
Ile Val Leu Lys Gly Ser Gly Lys Ile Ser Asp Arg Val Ile Leu Leu
705                 710                 715                 720
Thr Glu Tyr Asp Pro Arg Lys His Lys Tyr Asp Pro Asp Tyr Tyr Ile
                725                 730                 735
Glu Asn Gln Val Leu Pro Ala Val Leu Arg Ile Leu Glu Ala Phe Gly
                740                 745                 750
Tyr Arg Lys Glu Asp Leu Arg Tyr Gln Ser Ser Lys Gln Thr Gly Leu
                755                 760                 765
Asp Ala Trp Leu Lys Arg
        770

<210> SEQ ID NO 5
<211> LENGTH: 775
<212> TYPE: PRT
<213> ORGANISM: Pyrococcus sp. GB-D

<400> SEQUENCE: 5

Met Ile Leu Asp Ala Asp Tyr Ile Thr Glu Asp Gly Lys Pro Ile Ile
1               5                   10                  15
Arg Ile Phe Lys Lys Glu Asn Gly Glu Phe Lys Val Glu Tyr Asp Arg
                20                  25                  30
Asn Phe Arg Pro Tyr Ile Tyr Ala Leu Leu Lys Asp Asp Ser Gln Ile
            35                  40                  45
```

```
Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                    85                  90                  95

Arg Asp Lys Ile Arg Glu His Ser Ala Val Ile Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
        130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460
```

-continued

```
Lys Arg Lys Met Lys Ala Ser Lys Asp Pro Ile Glu Lys Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Arg Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
                580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
        610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Ile Lys Lys Lys
770                 775

<210> SEQ ID NO 6
<211> LENGTH: 776
<212> TYPE: PRT
<213> ORGANISM: Thermococcus sp. JDF-3

<400> SEQUENCE: 6

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60
```

```
Val Lys Arg Ala Glu Lys Val Lys Lys Phe Leu Gly Arg Ser Val
 65                  70                  75                  80

Glu Val Trp Val Leu Tyr Phe Thr His Pro Gln Asp Val Pro Ala Ile
                 85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Glu Glu Leu Lys Leu Met Ser Phe Asp Ile Glu Thr
            130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Ser Thr Glu Lys Glu Met Ile Lys
            180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Thr Ala Trp Glu Thr Gly Glu Gly
290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asn Leu Leu Glu Glu Arg Gln Lys Ile Lys
            450                 455                 460

Arg Lys Met Lys Ala Thr Leu Asp Pro Leu Glu Lys Asn Leu Leu Asp
465                 470                 475                 480
```

```
Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
            755                 760                 765

Leu Lys Pro Lys Gly Lys Lys Lys
            770                 775

<210> SEQ ID NO 7
<211> LENGTH: 775
<212> TYPE: PRT
<213> ORGANISM: Thermococcus sp. 9oN-7

<400> SEQUENCE: 7

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80
```

```
Glu Val Trp Lys Leu Tyr Phe Asn His Pro Gln Asp Val Pro Ala Ile
             85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Asp Ile Glu Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
            210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
            485                 490                 495
```

```
Tyr Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 8
<211> LENGTH: 774
<212> TYPE: PRT
<213> ORGANISM: Thermococcus sp. KS-1

<400> SEQUENCE: 8

Met Ile Leu Asp Thr Asp Tyr Ile Thr Glu Asn Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Ile Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Ala Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95
```

-continued

```
Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ala
                165                 170                 175

Asp Leu Pro Tyr Val Asp Val Val Ser Thr Glu Arg Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Lys Leu Gly Ile Asn Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Ala Thr Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510
```

```
Val Thr Ala Trp Gly Arg Glu Tyr Ile Thr Met Thr Ile Arg Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Gly Thr
    770

<210> SEQ ID NO 9
<211> LENGTH: 774
<212> TYPE: PRT
<213> ORGANISM: Thermococcus celer

<400> SEQUENCE: 9

Met Ile Leu Asp Ala Asp Tyr Ile Thr Glu Asp Gly Lys Pro Val Val
1               5                   10                  15

Arg Ile Phe Arg Lys Glu Lys Gly Glu Phe Arg Ile Asp Tyr Asp Arg
            20                  25                  30

Asp Phe Glu Pro Tyr Ile Tyr Ala Leu Leu Lys Asp Asp Ser Ala Ile
        35                  40                  45

Glu Glu Val Lys Arg Ile Thr Val Glu Arg His Gly Lys Ala Val Arg
    50                  55                  60

Val Lys Arg Val Glu Lys Val Lys Lys Phe Leu Asn Arg Pro Ile
65                  70                  75                  80

Glu Val Trp Lys Leu Tyr Phe Asn His Pro Gln Asp Val Pro Ala Ile
                85                  90                  95

Arg Asp Glu Ile Arg Lys His Pro Ala Val Val Asp Ile Tyr Glu Tyr
            100                 105                 110
```

```
Asp Ile Pro Phe Ala Lys Arg Tyr Leu Ile Asp Lys Gly Leu Val Pro
        115                 120                 125

Met Glu Gly Glu Glu Leu Lys Leu Met Ala Phe Asp Ile Glu Thr
    130                 135                 140

Leu Tyr His Glu Gly Asp Glu Phe Gly Glu Gly Pro Ile Leu Met Ile
145                 150                 155                 160

Ser Tyr Ala Asp Gly Asp Gly Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Gln Val Val Lys Glu Lys Asp Pro Asp Val Leu Val Thr
        195                 200                 205

Tyr Asn Gly Asp Asn Phe Asp Phe Ala Tyr Leu Lys Arg Arg Ser Glu
    210                 215                 220

Glu Leu Gly Leu Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Val Asn Leu Pro Thr
            260                 265                 270

Tyr Thr Leu Glu Ala Val Tyr Glu Ala Ile Phe Gly Arg Pro Lys Glu
        275                 280                 285

Lys Val Tyr Ala Gly Glu Ile Val Glu Ala Trp Glu Thr Gly Glu Gly
    290                 295                 300

Leu Glu Arg Val Ala Arg Tyr Ser Met Glu Asp Ala Lys Val Thr Phe
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Ser Gly Arg Glu Val Glu Ile Arg Arg Arg Gly Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Asn Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Gly Leu Leu Glu Glu Arg Gln Lys Ile Lys
    450                 455                 460

Arg Arg Met Lys Ala Ser Val Asp Pro Val Glu Arg Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Asp Arg Val Ile Arg Glu Leu
        515                 520                 525
```

```
Glu Glu Lys Phe Gly Phe Lys Val Leu Tyr Ala Asp Thr Asp Gly Leu
            530                 535                 540
His Ala Thr Ile Pro Gly Ala Asp Ala Gly Thr Val Lys Glu Arg Ala
545                 550                 555                 560
Arg Gly Phe Leu Arg Tyr Ile Asn Pro Lys Leu Pro Gly Leu Leu Glu
                565                 570                 575
Leu Glu Tyr Glu Gly Phe Tyr Leu Arg Gly Phe Phe Val Thr Lys Lys
            580                 585                 590
Lys Tyr Ala Val Ile Asp Glu Gly Lys Ile Thr Thr Arg Gly Leu
            595                 600                 605
Glu Ile Val Arg Arg Asp Trp Ser Glu Val Ala Lys Glu Thr Gln Ala
    610                 615                 620
Arg Val Leu Glu Ala Ile Leu Arg His Gly Asp Val Glu Glu Ala Val
625                 630                 635                 640
Arg Ile Val Arg Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Gly
            675                 680                 685
Arg Gly Val Arg Ile Arg Pro Gly Thr Val Ile Ser Tyr Ile Val Leu
690                 695                 700
Lys Gly Ser Gly Arg Ile Gly Asp Arg Ala Ile Pro Phe Asp Glu Phe
705                 710                 715                 720
Asp Pro Thr Lys His Arg Tyr Asp Ala Asp Tyr Tyr Ile Glu Asn Gln
                725                 730                 735
Val Leu Pro Ala Val Glu Arg Ile Leu Lys Ala Phe Gly Tyr Arg Lys
            740                 745                 750
Glu Asp Leu Lys Tyr Gln Lys Thr Arg Gln Val Gly Leu Gly Ala Trp
            755                 760                 765
Leu Asn Ala Gly Lys Gly
    770

<210> SEQ ID NO 10
<211> LENGTH: 775
<212> TYPE: PRT
<213> ORGANISM: Thermococcus siculi

<400> SEQUENCE: 10

Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Glu Tyr Asp Arg
            20                  25                  30
Thr Phe Glu Pro Tyr Ile Tyr Ala Leu Leu Lys Asp Asp Ser Ala Ile
        35                  40                  45
Glu Asp Val Lys Lys Ile Thr Ala Glu Arg His Gly Thr Val Val Lys
    50                  55                  60
Val Lys Arg Ala Glu Lys Val Gln Lys Lys Phe Leu Gly Arg Pro Val
65                  70                  75                  80
Glu Val Trp Lys Leu Tyr Phe Thr His Pro Gln Asp Val Pro Ala Ile
                85                  90                  95
Arg Asp Lys Ile Arg Lys His Pro Ala Val Ile Asp Ile Tyr Glu Tyr
            100                 105                 110
Asp Ile Pro Phe Ala Lys Arg Tyr Leu Ile Asp Lys Gly Leu Ile Pro
        115                 120                 125
```

```
Met Glu Gly Glu Glu Leu Lys Met Leu Ala Phe Asp Ile Glu Thr
    130                 135                 140

Leu Tyr His Glu Gly Glu Phe Ala Glu Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Leu Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Met Leu Glu Ala Val Tyr Glu Ala Ile Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Lys Val Thr Phe
305                 310                 315                 320

Glu Leu Gly Lys Glu Phe Phe Pro Met Glu Ala Gln Leu Ser Arg Leu
                325                 330                 335

Val Gly Gln Ser Phe Trp Asp Val Ala Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Ser Gly Arg Glu Tyr Asp Glu Arg Arg Gly Gly Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Ile Asp Pro Ile Glu Arg Lys Leu Leu Asp
465                 470                 475                 480

Tyr Arg Gln Arg Ala Ile Lys Ile Leu Leu Asn Ser Phe Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Arg Glu Ile
        515                 520                 525

Glu Glu Lys Tyr Gly Phe Lys Val Leu Tyr Ala Asp Thr Asp Gly Phe
    530                 535                 540
```

```
Phe Ala Thr Ile Pro Gly Glu Asp Ala Glu Thr Ile Lys Lys Arg Ala
545                 550                 555                 560

Met Glu Phe Leu Lys Tyr Ile Asn Ala Lys Leu Pro Gly Ala Leu Glu
            565                 570                 575

Leu Glu Tyr Glu Asp Phe Tyr Arg Arg Gly Phe Phe Val Thr Lys Lys
        580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Glu Ala Val
625                 630                 635                 640

Ser Ile Val Lys Glu Val Thr Glu Lys Leu Ser Lys Tyr Glu Val Pro
            645                 650                 655

Pro Glu Lys Leu Val Ile His Glu Gln Ile Thr Arg Glu Leu Lys Asp
        660                 665                 670

Tyr Lys Ala Thr Gly Pro His Val Ala Ile Ala Lys Arg Leu Ala Ala
    675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
            725                 730                 735

Val Leu Pro Ala Val Glu Arg Ile Leu Lys Ala Phe Gly Tyr Arg Gly
        740                 745                 750

Glu Glu Leu Arg Tyr Gln Lys Thr Arg Gln Val Gly Leu Gly Ala Trp
    755                 760                 765

Leu Lys Pro Lys Gly Lys Gly
770                 775

<210> SEQ ID NO 11
<211> LENGTH: 2325
<212> TYPE: DNA
<213> ORGANISM: Thermococcus kodakaraensis

<400> SEQUENCE: 11
atgatcctcg acactgacta cataaccgag gatggaaagc ctgtcataag aattttcaag    60
aaggaaaacg gcgagtttaa gattgagtac gaccggactt ttgaacccta cttctacgcc   120
ctcctgaagg acgattctgc cattgaggaa gtcaagaaga taccgccga gaggcacggg    180 acggttgtaa cggttaagcg ggttgaaaag gttcagaaga gttcctcgg gagaccagtt    240 gaggtctgga aactctactt tactcatccg caggacgtcc cagcgataag ggacaagata    300
cgagagcatc cagcagttat tgacatctac gagtacgaca tacccttcgc caagcgctac    360
ctcatagaca agggattagt gccaatggaa ggcgacgagg agctgaaaat gctcgccttc    420
gacattgaaa ctctctacca tgagggcgag gagttcgccg agggcccaat ccttatgata    480
agctacgccg acgaggaagg ggccagggtg ataacttgga gaacgtgga tctcccctac    540 gttgacgtcg tctcgacgga gagggagatg ataaagcgct tcctccgtgt tgtgaaggag    600
aaagacccgg acgttctcat aacctacaac ggcgacaact tcgacttcgc ctatctgaaa    660
aagcgctgtg aaaagctcgg aataaacttc gccctcggaa gggatggaag cgagccgaag    720
attcagagga tgggcgacag gtttgccgtc gaagtgaagg gacggataca cttcgatctc    780
```

```
tatcctgtga taagacggac gataaacctg cccacataca cgcttgaggc cgtttatgaa    840
gccgtcttcg gtcagccgaa ggagaaggtt tacgctgagg aaataaccac agcctgggaa    900
accggcgaga accttgagag agtcgcccgc tactcgatgg aagatgcgaa ggtcacatac    960
gagcttggga aggagttcct tccgatggag gcccagcttt ctcgcttaat cggccagtcc   1020
ctctgggacg tctcccgctc cagcactggc aacctcgttg agtggttcct cctcaggaag   1080
gcctatgaga ggaatgagct ggccccgaac aagcccgatg aaaaggagct ggccagaaga   1140
cggcagagct atgaaggagg ctatgtaaaa gagcccgaga gagggttgtg ggagaacata   1200
gtgtacctag attttagatc cctgtacccc tcaatcatca tcacccacaa cgtctcgccg   1260
gatacgctca acagagaagg atgcaaggaa tatgacgttg ccccacaggt cggccaccgc   1320
ttctgcaagg acttcccagg atttatcccg agcctgcttg agacctcct agaggagagg   1380 cagaagataa agaagaagat gaaggccacg attgacccga tcgagaggaa gctcctcgat   1440
tacaggcaga gggccatcaa gatcctggca acagctact acggttacta cggctatgca   1500
agggcgcgct ggtactgcaa ggagtgtgca gagagcgtaa cggcctgggg aagggagtac   1560
ataacgatga ccatcaagga gatagaggaa agtacggct ttaaggtaat ctacagcgac   1620
accgacggat tttttgccac aatacctgga gccgatgctg aaaccgtcaa aaagaaggct   1680
atggagttcc tcaagtatat caacgccaaa cttccgggcg cgcttgagct cgagtacgag   1740
ggcttctaca aacgcggctt cttcgtcacg aagaagaagt atgcggtgat agacgaggaa   1800
ggcaagataa caacgcgcgg acttgagatt gtgaggcgtg actggagcga gatagcgaaa   1860
gagacgcagg cgagggttct tgaagctttg ctaaaggacg gtgacgtcga aaggccgtg   1920 aggatagtca agaagttac cgaaaagctg agcaagtacg aggttccgcc ggagaagctg   1980
gtgatccacg agcagataac gagggattta aaggactaca aggcaaccgg tccccacgtt   2040
gccgttgcca agaggttggc cgcgagagga gtcaaaatac gccctggaac ggtgataagc   2100
tacatcgtgc tcaagggctc tgggaggata ggcgacaggg cgataccgtt cgacgagttc   2160
gacccgacga agcacaagta cgacgccgag tactacattg agaaccaggt tctcccagcc   2220
gttgagagaa ttctgagagc cttcggttac cgcaaggaag acctgcgcta ccagaagacg   2280
agacaggttg gtttgagtgc ttggctgaag ccgaagggaa cttga                   2325
```

<210> SEQ ID NO 12
<211> LENGTH: 2328
<212> TYPE: DNA
<213> ORGANISM: Pyrococcus furiosus

<400> SEQUENCE: 12

```
atgattttag atgtggatta cataactgaa gaaggaaaac ctgttattag gctattcaaa     60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga gaattgttga tgtagagaag gttgagaaaa gtttctcgg caagcctatt    240 accgtgtgga aactttattt ggaacatccc caagatgttc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gatatagaaa ccctctatca cgaaggagaa gagtttggaa aaggcccaat tataatgatt    480
agttatgcag atgaaaatga agcaaggtg attacttgga aaaacataga tcttccatac    540
gttgaggttg tatcaagcga gagagagatg ataaagagat ttctcaggat tatcagggag    600
```

```
aaggatcctg acattatagt tacttataat ggagactcat tcgcattccc atatttagcg    660
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaattttg gaaagccaaa ggagaaggta tacgccgacg agatagcaaa agcctgggaa     900
agtggagaga accttgagag agttgccaaa tactcgatgg aagatgcaaa ggcaacttat    960
gaactcggga aagaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggaaaac   1200
atagtatacc tagatttag agccctatat ccctcgatta taattaccca caatgtttct    1260
cccgatactc taaatcttga gggatgcaag aactatgata tcgctcctca gtaggccac    1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg ggaagaaag    1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca tggagaacca ggttcttcca   2220
gcggtactta ggatattgga gggatttgga tacagaaagg aagacctcag ataccaaaag   2280
acaagacaag tcggcctaac ttcctggctt aacattaaaa aatcctag                2328
```

<210> SEQ ID NO 13
<211> LENGTH: 22
<212> TYPE: DNA
<213> ORGANISM: Artificial sequence
<220> FEATURE:
<223> OTHER INFORMATION: Primer

<400> SEQUENCE: 13
ataaccgagg atggaaagcc tg                                              22

<210> SEQ ID NO 14
<211> LENGTH: 21
<212> TYPE: DNA
<213> ORGANISM: Artificial sequence
<220> FEATURE:
<223> OTHER INFORMATION: Primer

```
<400> SEQUENCE: 14
ggcgtcagtg tcgaggatca t                                          21

<210> SEQ ID NO 15
<211> LENGTH: 24
<212> TYPE: DNA
<213> ORGANISM: Artificial sequence
<220> FEATURE:
<223> OTHER INFORMATION: Primer

<400> SEQUENCE: 15
cactacttct acgccctcct gaag                                       24

<210> SEQ ID NO 16
<211> LENGTH: 24
<212> TYPE: DNA
<213> ORGANISM: Artificial sequence
<220> FEATURE:
<223> OTHER INFORMATION: Primer

<400> SEQUENCE: 16
aaatacttct acgccctcct gaag                                       24

<210> SEQ ID NO 17
<211> LENGTH: 24
<212> TYPE: DNA
<213> ORGANISM: Artificial sequence
<220> FEATURE:
<223> OTHER INFORMATION: Primer

<400> SEQUENCE: 17
cgttacttct acgccctcct gaag                                       24

<210> SEQ ID NO 18
<211> LENGTH: 25
<212> TYPE: DNA
<213> ORGANISM: Artificial sequence
<220> FEATURE:
<223> OTHER INFORMATION: Primer

<400> SEQUENCE: 18
ttcaaaagtc cggtcgtact caatc                                      25

<210> SEQ ID NO 19
<211> LENGTH: 25
<212> TYPE: DNA
<213> ORGANISM: Artificial sequence
<220> FEATURE:
<223> OTHER INFORMATION: Primer

<400> SEQUENCE: 19
ctgcggatga gtaaagtaga gtttc                                      25

<210> SEQ ID NO 20
<211> LENGTH: 31
<212> TYPE: DNA
<213> ORGANISM: Artificial sequence
<220> FEATURE:
<223> OTHER INFORMATION: Primer

<400> SEQUENCE: 20
gaccagccag cgataaggga caagatacga g                               31

<210> SEQ ID NO 21
<211> LENGTH: 31
```

```
<212> TYPE: DNA
<213> ORGANISM: Artificial sequence
<220> FEATURE:
<223> OTHER INFORMATION: Primer

<400> SEQUENCE: 21
gacaaaccag cgataaggga caagatacga g                                   31

<210> SEQ ID NO 22
<211> LENGTH: 31
<212> TYPE: DNA
<213> ORGANISM: Artificial sequence
<220> FEATURE:
<223> OTHER INFORMATION: Primer

<400> SEQUENCE: 22
gaccgtccag cgataaggga caagatacga g                                   31

<210> SEQ ID NO 23
<211> LENGTH: 22
<212> TYPE: DNA
<213> ORGANISM: Artificial sequence
<220> FEATURE:
<223> OTHER INFORMATION: Primer

<400> SEQUENCE: 23
gacatattcg ccaagcgcta cc                                             22

<210> SEQ ID NO 24
<211> LENGTH: 26
<212> TYPE: DNA
<213> ORGANISM: Artificial sequence
<220> FEATURE:
<223> OTHER INFORMATION: Primer

<400> SEQUENCE: 24
gtactcgtag atgtcaataa ctgctg                                         26

<210> SEQ ID NO 25
<211> LENGTH: 22
<212> TYPE: DNA
<213> ORGANISM: Artificial sequence
<220> FEATURE:
<223> OTHER INFORMATION: Primer

<400> SEQUENCE: 25
ttaggcctta gcgggcttag ac                                             22

<210> SEQ ID NO 26
<211> LENGTH: 22
<212> TYPE: DNA
<213> ORGANISM: Artificial sequence
<220> FEATURE:
<223> OTHER INFORMATION: Primer

<400> SEQUENCE: 26
ccaggatttt tgatgggaca cg                                             22

<210> SEQ ID NO 27
<211> LENGTH: 23
<212> TYPE: DNA
<213> ORGANISM: Artificial sequence
<220> FEATURE:
<223> OTHER INFORMATION: Primer

<400> SEQUENCE: 27
```

-continued aatactgcgc tcttccaaca agc                                    23

<210> SEQ ID NO 28
<211> LENGTH: 23
<212> TYPE: DNA
<213> ORGANISM: Artificial sequence
<220> FEATURE:
<223> OTHER INFORMATION: Primer

<400> SEQUENCE: 28
taccagccat gtgaggtgtc agt                                    23

<210> SEQ ID NO 29
<211> LENGTH: 22
<212> TYPE: DNA
<213> ORGANISM: Artificial sequence
<220> FEATURE:
<223> OTHER INFORMATION: Primer

<400> SEQUENCE: 29
gctgctctgt gcatccgagt gg                                     22

<210> SEQ ID NO 30
<211> LENGTH: 22
<212> TYPE: DNA
<213> ORGANISM: Artificial sequence
<220> FEATURE:
<223> OTHER INFORMATION: Primer

<400> SEQUENCE: 30
ggtgttccct tgatgtagca ca                                     22

<210> SEQ ID NO 31
<211> LENGTH: 26
<212> TYPE: DNA
<213> ORGANISM: Artificial sequence
<220> FEATURE:
<223> OTHER INFORMATION: Primer

<400> SEQUENCE: 31
acatgtattt gcatggaaaa caactc                                 26

<210> SEQ ID NO 32
<211> LENGTH: 21
<212> TYPE: DNA
<213> ORGANISM: Artificial sequence
<220> FEATURE:
<223> OTHER INFORMATION: Primer

<400> SEQUENCE: 32
ataactgaag aaggaaaacc t                                      21

<210> SEQ ID NO 33
<211> LENGTH: 21
<212> TYPE: DNA
<213> ORGANISM: Artificial sequence
<220> FEATURE:
<223> OTHER INFORMATION: Primer

<400> SEQUENCE: 33
ggcatccaca tctaaaatca t                                      21

<210> SEQ ID NO 34
<211> LENGTH: 23
<212> TYPE: DNA
<213> ORGANISM: Artificial sequence

```
<220> FEATURE:
<223> OTHER INFORMATION: Primer

<400> SEQUENCE: 34
cactacattt acgctcttct cag                                             23

<210> SEQ ID NO 35
<211> LENGTH: 25
<212> TYPE: DNA
<213> ORGANISM: Artificial sequence
<220> FEATURE:
<223> OTHER INFORMATION: Primer

<400> SEQUENCE: 35
tctaaaagtt ctatcatgct ctatc                                           25

<210> SEQ ID NO 36
<211> LENGTH: 26
<212> TYPE: DNA
<213> ORGANISM: Artificial sequence
<220> FEATURE:
<223> OTHER INFORMATION: Primer

<400> SEQUENCE: 36
aaacccacta ttagagaaaa agttag                                          26

<210> SEQ ID NO 37
<211> LENGTH: 24
<212> TYPE: DNA
<213> ORGANISM: Artificial sequence
<220> FEATURE:
<223> OTHER INFORMATION: Primer

<400> SEQUENCE: 37
atcttgggga tgttccaaat aaag                                            24

<210> SEQ ID NO 38
<211> LENGTH: 23
<212> TYPE: DNA
<213> ORGANISM: Artificial sequence
<220> FEATURE:
<223> OTHER INFORMATION: Primer

<400> SEQUENCE: 38
gacggagact cattcgcatt ccc                                             23

<210> SEQ ID NO 39
<211> LENGTH: 24
<212> TYPE: DNA
<213> ORGANISM: Artificial sequence
<220> FEATURE:
<223> OTHER INFORMATION: Primer

<400> SEQUENCE: 39
ataagtaact ataatgtcag gatc                                            24

<210> SEQ ID NO 40
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is I
<220> FEATURE:
```

```
<221> NAME/KEY: modified_base
<222> LOCATION: (18)..(18)
<223> OTHER INFORMATION: n is I

<400> SEQUENCE: 40
atggarytnt tygaygwnca                                               20

<210> SEQ ID NO 41
<211> LENGTH: 21
<212> TYPE: DNA
<213> ORGANISM: Artificial sequence
<220> FEATURE:
<223> OTHER INFORMATION: Primer
<220> FEATURE:
<221> NAME/KEY: modified_base
<222> LOCATION: (7)..(7)
<223> OTHER INFORMATION: n is I
<220> FEATURE:
<221> NAME/KEY: modified_base
<222> LOCATION: (10)..(10)
<223> OTHER INFORMATION: n is I

<400> SEQUENCE: 41
ytaytgnggn arytgccart c                                             21

<210> SEQ ID NO 42
<211> LENGTH: 20
<212> TYPE: DNA
<213> ORGANISM: Artificial sequence
<220> FEATURE:
<223> OTHER INFORMATION: Primer

<400> SEQUENCE: 42
aagagagggt tggagagtag                                               20

<210> SEQ ID NO 43
<211> LENGTH: 24
<212> TYPE: DNA
<213> ORGANISM: Artificial sequence
<220> FEATURE:
<223> OTHER INFORMATION: Primer

<400> SEQUENCE: 43
cccctaaaaa aaaaatcaaa aatc                                          24

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
gagttggtga tgttagatta g                                             21

<210> SEQ ID NO 45
<211> LENGTH: 22
<212> TYPE: DNA
<213> ORGANISM: Artificial sequence
<220> FEATURE:
<223> OTHER INFORMATION: Primer

<400> SEQUENCE: 45
ttcccaaaaa aatcccaaat tc                                            22
```

```
<210> SEQ ID NO 46
<211> LENGTH: 19
<212> TYPE: DNA
<213> ORGANISM: Artificial sequence
<220> FEATURE:
<223> OTHER INFORMATION: Primer

<400> SEQUENCE: 46
agagaggagt ttagattgg                                              19

<210> SEQ ID NO 47
<211> LENGTH: 21
<212> TYPE: DNA
<213> ORGANISM: Artificial sequence
<220> FEATURE:
<223> OTHER INFORMATION: Primer

<400> SEQUENCE: 47
caaaaaaact aaaacctcaa c                                           21

<210> SEQ ID NO 48
<211> LENGTH: 25
<212> TYPE: DNA
<213> ORGANISM: Artificial sequence
<220> FEATURE:
<223> OTHER INFORMATION: Primer

<400> SEQUENCE: 48
tttatttata taattttgtg tatgg                                       25

<210> SEQ ID NO 49
<211> LENGTH: 21
<212> TYPE: DNA
<213> ORGANISM: Artificial sequence
<220> FEATURE:
<223> OTHER INFORMATION: Primer

<400> SEQUENCE: 49
cacccctcac tttactaaaa c                                           21

<210> SEQ ID NO 50
<211> LENGTH: 22
<212> TYPE: DNA
<213> ORGANISM: Artificial sequence
<220> FEATURE:
<223> OTHER INFORMATION: Primer

<400> SEQUENCE: 50
ggtgttccct tgatgtagca ca                                          22

<210> SEQ ID NO 51
<211> LENGTH: 23
<212> TYPE: DNA
<213> ORGANISM: Artificial sequence
<220> FEATURE:
<223> OTHER INFORMATION: Primer

<400> SEQUENCE: 51
attacctacc tttctggttg att                                         23
```